United States Patent
Liu et al.

(10) Patent No.: US 6,461,622 B2
(45) Date of Patent: *Oct. 8, 2002

(54) TOPICAL COMPOSITIONS

(75) Inventors: Jue-Chen Liu, Neshanic; Jonas C. T. Wang, Robbinsville; Mohammed Yusuf, Edison, all of NJ (US); Norihiro Yamamoto, Koriyama; Satoshi Kazama, Sukagawa, both of (JP); Christopher R. Stahl, Hawthorne, CA (US); Jean P. Holland, Doylestown, PA (US); Kamran Mather, Agoura Hills, CA (US); Margaret A. Aleles, Gladstone, NJ (US); Sachio Hamada, St. Germain (GB); Curtis A. Cole, Langhorne; Stephen J. Wisniewski, Doylestown, both of PA (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/807,351

(22) Filed: Feb. 27, 1997

(65) Prior Publication Data

US 2001/0055597 A1 Dec. 27, 2001

Related U.S. Application Data

(63) Continuation of application No. 08/609,588, filed on Mar. 1, 1996, now Pat. No. 5,976,555, and a continuation of application No. 08/523,836, filed on Sep. 6, 1995, now Pat. No. 6,080,393.

(51) Int. Cl.[7] .................................................. A61K 6/00
(52) U.S. Cl. .......................... 424/401; 424/60; 424/59; 514/844; 514/847; 514/887; 514/772.6; 514/941; 514/938
(58) Field of Search ........................... 424/401, 60, 59, 424/195.1, 783; 514/844, 847, 887, 772.6, 941, 938

(56) References Cited

U.S. PATENT DOCUMENTS

| | | |
|---|---|---|
| 2,897,119 A | 7/1959 | Dunn et al. |
| 3,906,108 A | 9/1975 | Felty |
| 4,214,000 A | 7/1980 | Papa |
| 4,247,547 A | 1/1981 | Marks |

(List continued on next page.)

FOREIGN PATENT DOCUMENTS

| | | |
|---|---|---|
| DE | 29 20 456 | 5/1978 |
| DE | 3514724 C2 | 10/1986 |
| EP | 0 408 370 B1 | 1/1981 |
| EP | 0 094 771 B1 | 11/1983 |

(List continued on next page.)

OTHER PUBLICATIONS copy of packaging of product Retin–A–Gel (tretinoin) 0.01% and enclosed pamphlet 1989.
copy of packaging of product Retin–A–Gel (tretinoin) 0.025% and enclosed pamphlet 1989.

(List continued on next page.)

Primary Examiner—Thurman K. Page
Assistant Examiner—Lakshmi Channavajjala

(57) ABSTRACT

Skin care compositions comprising an oil-in-water emulsion base containing retinoids and possessing good physical and chemical stability.

44 Claims, 5 Drawing Sheets

U.S. PATENT DOCUMENTS

| | | | |
|---|---|---|---|
| 4,333,924 A | 6/1982 | Bowley et al. | |
| 4,466,805 A | 8/1984 | Welters et al. | |
| 4,551,480 A | 11/1985 | Stiefel et al. | |
| 4,595,586 A | 6/1986 | Flom | |
| 4,603,146 A | 7/1986 | Kligman | |
| 4,720,353 A | 1/1988 | Bell | |
| 4,826,828 A | 5/1989 | Wilmott et al. | |
| 4,877,805 A | 10/1989 | Kligman | |
| 5,023,235 A | 6/1991 | N'Guyen et al. | |
| 5,034,228 A | 7/1991 | Meybeck et al. | |
| 5,302,376 A * | 4/1994 | Forestier et al. | 424/59 |
| 5,391,373 A | 2/1995 | Mausner | |
| 5,484,816 A * | 1/1996 | Yanagida et al. | 514/725 |
| 5,559,149 A | 9/1996 | Clum et al. | |
| 5,616,332 A * | 4/1997 | Herstein | 424/401 |
| 5,646,186 A * | 7/1997 | Wang et al. | 514/557 |
| 5,652,263 A | 7/1997 | Clum et al. | |
| 5,958,431 A | 9/1999 | Brancq et al. | |
| 5,976,555 A | 11/1999 | Liu et al. | |
| 6,024,941 A | 2/2000 | Yanigada et al. | |
| 6,080,393 A | 6/2000 | Liu et al. | |
| 6,193,956 B1 | 2/2001 | Liu et al. | |

FOREIGN PATENT DOCUMENTS

| | | |
|---|---|---|
| EP | 0 330 496 | 8/1989 |
| EP | 0 343 444 | 12/1989 |
| EP | 0 391 033 A2 | 10/1990 |
| EP | 0 421 333 A1 | 4/1991 |
| EP | 0 440 398 A1 | 7/1991 |
| EP | 0 508 848 B1 | 10/1992 |
| EP | 0 608 433 A1 | 1/1994 |
| EP | 0 580 968 B1 | 2/1994 |
| EP | 0 586 106 A1 | 9/1994 |
| EP | 0 631 772 A2 | 4/1995 |
| EP | 0 666 735 B1 | 8/1995 |
| FR | 3400 M | 6/1965 |
| FR | 2 633 515 | 5/1990 |
| FR | 2 714 595 | 7/1995 |
| FR | 2 732 595 | 11/1996 |
| GB | 2 304 573 A | 3/1997 |
| JP | 53 14607 | 5/1978 |
| JP | 58 41813 | 3/1983 |
| WO | WO 93/00085 | 7/1993 |
| WO | WO 94/07478 | 4/1994 |
| WO | WO 94/21217 | 9/1994 |
| WO | WO 95/25507 | 9/1995 |
| WO | WO 95/26709 A1 | 10/1995 |
| WO | WO 96/07396 A2 | 3/1996 |

OTHER PUBLICATIONS copy of packaging of product Retin–A Liquid (tretinoin) 0.05% and enclosed pamphlet 1979.
copy of packaging of product Retin–A Cream (tretinoin) 0.1% and enclosed pamphlet 1989.
copy of packaging Retin–A Cream (tretinoin) 0.025% and enclosed pamphlet 1989.
copy of packaging Retin–A Cream (tretinoin) 0.05% and enclosed pamphlet 1989.
copy of packaging Retin–A Micro (tretinoin gel) microsphere, 0.1% and enclosed pamphlet 1997.
copy of packaging Renova (tretinoin emollient cream) 0.05% and enclosed pamphlet 1991.
copy of Renova (tretinoin emollient cream) 0.05% guide to success pamphlet 1997.
Prescription Pharmacy, $2^{nd}$ Ed., (1970) J.B. Sprowls, Jr., p. 220–223.
Product Data Sheet for Vitamin A Alcohol Blend, Roche, 1988.
Buhker, V., Vademecum for Vitamin Formulations, 1988.
Dittert, L.W. Sprowls' American Pharmacy, $7^{th}$ Ed., p. 471 (1974).
McCutcheon's Emulsifier's and Detergents, vol. 1 p. 250 (1991).
Remington's Pharmaceutical Sciences, $15^{th}$ Ed. (1975) p. 329–337.
PCT Search Report dated Nov. 20, 1997 for application PCT/US 97/03169.

* cited by examiner

TOPICAL COMPOSITIONS

This application is a continuation U.S. patent application Ser. Nos. 08/523,836 filed Sep. 6, 1995 now U.S. Pat. No. 6,080,393 and a continuation Ser. No. 08/609,588 filed Mar. 1, 1996 now U.S. Pat. No. 5,976,555 and Japanese Patent Application No. Hei 6-238639, filed Sep. 7, 1994 and from which this application claims the benefit of priority.

FIELD OF THE INVENTION

This invention relates to skin care compositions which may contain retinoids and other ingredients which generally improve the quality of the skin, particularly human facial skin. More particularly, the present invention relates to chemically stable skin care compositions comprising an oil-in-water emulsion and certain retinoids and to methods for making such compositions. This invention also relates to packaging and methods of packaging such compositions so as to preserve their chemical stability.

BACKGROUND OF THE INVENTION

Skin care compositions containing retinoids have become the focus of great interest in recent years. Retinoic acid, also known as Vitamin A acid or tretinoin, is well-known for the treatment of such skin conditions as acne and products containing retinoic acid are commercially available in various forms from the Dermatological Division of Ortho Pharmaceutical Corporation. Such products, for example, include Retin A* creams, an oil-in-water emulsion of retinoic acid containing as an oil-soluble antioxidant, butylated hydroxytoluene (BHT); Retin A* liquid, a solution of retinoic acid in a polyethylene glycol/ethanol solvent employing BHT as an antioxidant; and Retin A* gel, which comprises retinoic acid in a gel vehicle comprising ethyl alcohol as the solvent, hydroxypropyl cellulose as the thickener or gelling agent and BHT as an antioxidant. These retinoic acid containing products have proven stable and capable of providing active ingredients after extended periods of storage.

More recently, however, wider use of retinoids has been suggested for treatments other than acne such as, for example, the treatment of skin against photoaging and sun damage. Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are most prominent in light-skinned persons who burn easily and tan poorly. These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The problem of skin aging is addressed in U.S. Pat. No. 4,603,146, wherein Vitamin A acid in an emollient vehicle is suggested as a treatment. Further, in U.S. Pat. No. 4,877,805, it is suggested that a number of retinoids are useful for restoring and reversing sun damage of human skin.

When considering the use of retinoids in skin care products, it is believed that certain retinoids such as, for example, retinol (Vitamin A alcohol), retinal (Vitamin A aldehyde) and retinyl esters such as retinyl acetate and retinyl palmitate would be preferred over retinoic acid. This is because they are endogenous compounds naturally occurring in the human body and essential for good growth, differentiation of the epithelial tissues and reproduction. Additionally, excess retinol is stored in the human body largely in an inactive ester form, e.g., retinyl palmitate and, to some extent, retinyl acetate. The aldehyde, retinal, also a preferred form, is an active metabolite of retinol. Accordingly, attention has turned toward formulating skin care compositions which contain these preferred, naturally occurring retinoids.

In formulating products containing such retinoids, the same properties sought with respect to the retinoic acid formulas are desirable for other retinoid containing compositions. Specifically, much attention is directed toward providing a composition which is aesthetically pleasing and which can deliver active ingredients after a substantial shelf life. Not surprising, in formulating products containing such retinoids, the art is led to the experience gained in the already existing formulas containing retinoic acid. Typically, such formulas comprise oil-in-water emulsions wherein the retinoic acid is carried within the oil phase and is protected from oxidation by employing an oil-soluble antioxidant. With respect to the form of the emulsion, oil-in-water emulsions have been preferred in that, as compared to water-in-oil emulsions for example, they are non-occlusive, non-greasy, compatible with other such emulsion products, easy to remove from the skin and are regarded as more aesthetically pleasing as well as being more economical to manufacture. With respect to chemical stability of the active ingredient, it has been experienced that the retinoic acid in the oil phase is, in the main, well protected by including in such oil phase an oil soluble antioxidant.

Thus, various oil-in-water emulsions containing retinoic acid and BHT, as oil-soluble antioxidant have been described and sold, for example, in U.S. Pat. No. 3,906,108, U.S. Pat. No. 4,66,805, and U.S. Pat. No. 4,247,547. The retinoic acid containing compositions described in these patents have proven to be, or are said to be, chemically stable. Therefore, a number of skin care products have appeared in the marketplace incorporating other retinoids, including, for example, retinol, retinal and retinyl esters such as retinyl acetate and retinyl palmitate, and these unsurprisingly emulate the formulas of the commercial retinoic acid compositions, i.e., are oil-in-water emulsions protected by oil-soluble antioxidants. Unfortunately, it has been found that these other retinoids in such compositions quickly lose their activity and either oxidize or isomerize to non-efficacious chemical forms with the result that the amount of retinoid actually available to provide the beneficial effects of the product is reduced, in an unacceptably short period of time, to an ineffective quantity and eventually to only trace quantities.

There have been attempts to formulate a stable composition comprising retinol, retinal, retinyl acetate and retinyl palmitate in oil-in-water emulsions, such as in U.S. Pat. No. 4,826,828. Avon Products, Inc., the assignee of U.S. Pat. No. 4,826,828, sells two skin care products called Bioadvance and Bioadvance 2000. Each of these products is supplied in two bottles, portions of which are mixed together just prior to use. U.S. Pat. No. 4,720,353 (Bell) describes water-in-oil emulsion carriers for various medicaments and drugs intended for topical application to the skin. Other water-in-oil type emulsions have been described in EP 0 343 444 A2 (Siemer et al.) and EP 0 330 496 A2 (Batt).

Clum et al., in U.S. patent application Ser. No. 07/719,264, now abandoned, describe stable water-in-oil compositions containing a retinoid and a stabilizing system selected from the group consisting of: (a) a chelating agent and at least one oil-soluble antioxidant; (b) a chelating agent and at least one water-soluble antioxidant; and (c) an antioxidant present in each of the oil and water phases of the emulsion. This composition retains at least about 60% of the retinoids after 13 weeks of storage at 40° C. Although this system is quite stable and useful in retinoid-containing products, it is nevertheless a water-in-oil emulsion and retains all the attributes, advantages and disadvantages of such a formulation. It is therefore an object of this invention to provide an oil-in-water formulation which is stable and acceptable for use on the skin.

SUMMARY OF THE INVENTION

In accordance with the present invention, it has now been unexpectedly found that certain retinoids may be successfully stabilized against chemical degradation by incorporating them into oil-in-water emulsions comprising a specifically defined stabilizing system. In addition, this invention relates to oil-in-water emulsion compositions which are cosmetically elegant.

The retinoids which can be stabilized against chemical degradation in accordance with the principles of the present invention are retinol (Vitamin A alcohol), retinal (Vitamin A aldehyde), retinyl acetate, retinyl palmitate and mixtures thereof. It is also theorized that other retinoids, including synthetic retinoids and retinoid-like chemicals may benefit from inclusion in the formulations of this invention.

As used herein, the "chemical stability" or "stability" of a retinoid is defined in terms of the percentage of the specified retinoid which is retained in its original chemical form after the composition has been stored for a specified period of time at a specified temperature. Thus, if the original concentration of all-trans retinol in an absolute ethanol solution were 0.20% by weight and, after two (2) weeks' storage at room temperature (21° C.±1° C.), the concentration of all-trans retinol were 0.18% by weight, then the original solution would be characterized as having a chemical stability of 90% after two weeks' storage at room temperature. In the same fashion, if an emulsion comprising all-trans retinol had an initial concentration of 0.30% by weight and after storage for 13 weeks at 40° C. had a concentration of all trans-retinol of 0.24% by weight, then the original emulsion retinol of 80% after 13 weeks' storage at 40° C.

Specifically, a commercially usable composition should exhibit a stability of at least about 60% of the active retinoid(s) after 13 weeks storage at 40° C. Preferably, the compositions of this invention exhibit a stability of at least about 70% after 13 weeks' storage at 40° C.

Accordingly, there is provided, in accordance with the teachings of this invention, a skin care composition comprising an oil-in-water emulsion and a retinoid selected from the group consisting of retinol, retinal, retinyl acetate, retinyl palmitate and mixtures thereof, said composition having a pH of between about 4 and about 10; said composition further comprising an oil phase, said oil phase having a relatively low level of unsaturation; said composition further comprising a stabilizing system selected from the group consisting of:

a) at least one oil-soluble antioxidant;
b) a chelating agent and at least one oil-soluble antioxidant;
c) a chelating agent; and
d) a chelating agent and an antioxidant present in each of the oil and water phases of said emulsion; said composition retaining at least about 70% of said retinoids after 13 weeks' storage at 40° C.

Additionally, there are provided herein oil-in-water emulsions having novel emulsification systems. The oil-in-water emulsion compositions of this invention preferably contain:

a) an emulsifier system selected from the group consisting of:
   i) a mixture of glyceryl stearate and polyethylene glycol 100 stearate;
   ii) cetearyl alcohol and cetearyl glucoside;
   iii) a mixture of a polyethylene glycol ether of stearyl alcohol of the formula:

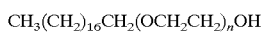

wherein n is 21 and a polyethylene glycol ether of stearyl alcohol of the formula:

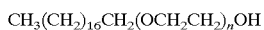

wherein n is 2; and
   iv) a mixture of sorbitan stearate and polysorbate 60 (a mixture of stearate esters of sorbitol and sorbitol anhydrides condensed with 20 moles of ethylene oxide);
b) a co-emulsifier selected from the group consisting of: cetyl alcohol, stearyl alcohol and mixtures thereof;
c) an oil phase present in the amount of from about 2 to about 20 percent by weight of the total emulsion composition comprising:
   i) a light, dry absorbable oil and
   ii) substantive, emollient oils or waxes
wherein such dry absorbable oil and such substantive emollient oil are present in a ratio of from about 1:3 to about 10:1.

DETAILED DESCRIPTION OF THE PREFERRED EMBODIMENTS

As described above, the composition of the invention is in the form of a particular type of emulsion, namely oil-in-water. As used herein, the generally accepted concept of an emulsion applies, i.e., an intimate mixture of two immiscible liquids which remains unseparated for an acceptable shelf life at or about room temperature. Ordinarily, when two immiscible liquids are mechanically agitated, both phases initially tend to form droplets. Thereafter, when the agitation ceases, the droplets quickly coalesce, and the two liquids tend to separate. On the other hand, an emulsion may be formed and physically stabilized and the lifetime of the droplets in intimate mixture materially increased if a compound, referred to as an emulsifier, is added to the immiscible liquids. Usually only one phase persists in droplet form for a prolonged period of time, and this is referred to as the internal phase which is surrounded by an external phase. An oil-in-water emulsion is one in which the external phase (also called the continuous phase) comprises water or an aqueous solution and the internal phase (also called the discontinuous or disperse phase) comprises an oil or mixture of mutually soluble oils.

A suitable vehicle for delivery of skin care active ingredients should combine a variety of features. It should be esthetically acceptable for its intended use, i.e. it should be compatible with other products including color cosmetics, it should be low or lacking in odor, easy to apply and spread, quickly absorbed and should leave a non-greasy but perceptibly functional residue. It should also be easily and quickly produced, cost-effective and have suitable physical stability under a variety of adverse conditions, such as high and low temperatures. It should also have a relatively long shelf life under normal commercial and residential environmental conditions.

The novel compositions of this invention should contain an esthetically acceptable oil phase composed of non-volatile compounds which remain on the skin after application. They should also contain an acceptable emulsification system which assists in maintaining the physical stability of the formulation. Surprisingly, the emulsification systems of this invention have been found to act to "balance" the esthetic appearance and feel of the compositions while maintaining the physical stability of the compositions.

The emulsifiers useful in the compositions of this invention may be chosen from the following: (i) a mixture of glyceryl stearate and polyethylene glycol 100 stearate (available commercially as Arlacel 165 from ICI Americas); (ii) cetearyl alcohol and cetearyl glucoside (preferably in combination with cetearyl alcohol), available commercially as Montanov 68 from SEPPIC; (iii) a mixture of a polyethylene glycol ether of stearyl alcohol of the formula:

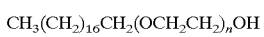

wherein n is 21 and a polyethylene glycol ether of stearyl alcohol of the formula:

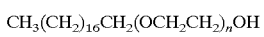

wherein n is 2 (available commercially as Brij 721 and Brij 72 from ICI Americas); and (iv) a mixture of sorbitan stearate and polysorbate 60 (a mixture of stearate esters of sorbitol and sorbitol anhydrides condensed with 20 moles of ethylene oxide), available commercially as, respectively, Span 60 and Tween 60 from ICI Americas.

Two particularly preferred emulsification systems include (a) a mixture of glyceryl stearate and polyethylene glycol 100 stearate and (b) cetearyl alcohol and cetearyl glucoside. These emulsification systems permit the water and oil phases to be combined such that the oil phase forms droplets in the water phase. When incorporating system (a) into a composition of this invention, the ratio of glyceryl stearate to polyethylene glycol 100 stearate should be from about 1:1. When incorporating system (b) into a composition of this invention, the ratio of cetearyl alcohol to cetearyl glucoside should be from about 6:1 to about 3:1. The amount of emulsifier present in the compositions of this invention should be from about 1 to about 10 weight percent. More preferably, from about 1 to about 6 weight percent should be used. Most preferably, from about 1 to about 5 weight percent should be used.

In order to maintain the droplets as separate entities, and to prevent the phases from separating, accessory emulsifiers or "co-emulsifiers" are often utilized. These co-emulsifiers prevent the oil phase from coalescing or creaming and keep the phases physically stable as an emulsion prior to application to the skin. They lend "body" to the emulsion and give the formulation its character as a lotion or a cream by imparting viscosity to the composition. It has been found that particularly useful co-emulsifiers are fatty alcohols such as cetyl and stearyl alcohols and the like. Preferably, a mixture of cetyl and stearyl alcohols should be used as the co-emulsifier in most cases. Preferably, the ratio of cetyl alcohol to stearyl alcohol should be from about 2:1 to about 1:2. Preferably, the co-emulsifier should compose from about 1 to about 5 weight percent of the composition. The preferred ratio of emulsifier to co-emulsifier is from about 3:1 to about 1:10. More preferably, the ratio should be from about 3:1 to about 1:3.

The present invention also provides oil-in-water emulsion compositions containing at least one retinoid compound wherein the physical stability of the emulsion and the chemical stability of the active ingredients are excellent. The present invention also provides a method for making such emulsion compositions and a method and apparatus for storing such emulsion compositions in order to maintain their stability during storage and prior to use by the consumer. It should be noted, however, that the base emulsion, including the emulsifiers, co-emulsifiers and oil phase, of this invention may be used not only in combination with retinoids, but with a variety of active topical ingredients with or without the inclusion of retinoid materials.

The skin care compositions of the present invention comprising an oil-in-water emulsion can be in the format of cream or lotion formulations, as desired, by varying the relative quantities of the oil and water phases of the emulsion. The pH of the compositions should be in the range of from about 4 to about 10; preferably they should be from about 6 to about 8. It has been found that, in compositions having a pH of about 6 or more, the retinoid is more stable than at pH of less than 6. Furthermore, the stability of the retinol is less dependent upon the actual materials used in the formulation at pH of 6 or more.

Preferably, the oils used in the compositions of this invention are relatively highly saturated, preferably those having a relatively low iodine value. The contribution to unsaturation, density C, of an individual oil in the composition is calculated as follows:

$$C = A \times B,$$

where A is the percentage of the unsaturated oil or fat used in an oil-in-water emulsion and B is the iodine value of the unsaturated oil. If a mixture of oils is used in the oil phase, the total unsaturation density will be the sum of all individual C values. Accordingly, an oil phase having an unsaturation density or total C of 1200 or less and preferably 500 or less should be used in the formulations of this invention. It is theorized that saturated oils and/or fats are less reactive than unsaturated oils and fats, due to the presence of reactive double bonds in unsaturated oils and fats, which can initiate reactions with the retinoids and other materials in the compositions of this invention. Synthetic oils that are useful are fatty acid esters, fatty alcohols, for example, octyl hydroxystearate, cetyl palmitate, cetyl alcohol, glyceryl stearate and PEG-100 stearate, stearyl alcohol, octyl pelargonate and the like. Examples of preferred oils are as follows: Finsolv TN (available from Finetex of New Jersey), Miglyol 812 (available from Huls Corporation of New York), silicone oil (Dow Corning of Michigan), mineral oil, and the like, having very low iodine values are also quite useful in the compositions of this invention. Furthermore, the percentage of the oil present in the compositions of this invention is also relevant: the lower the percentage of high-iodine value oil, the more stable the retinoid in the composition.

When the emulsion compositions of this invention are applied to the skin, the aqueous portions of the compositions volatilize, while the non-volatile portion of the compositions of this invention remain upon the skin. The oil phase components along with the co-emulsifiers and emulsifiers make up this non-volatile portion of the compositions. Thus, the esthetics of the non-volatile portion are quite important in making the compositions of this invention.

It is desirable to compose an oil phase containing both at least one "dry" absorbable emollient oil and at least one substantive oil or wax. A dry absorbable emollient oil is needed for the purpose of quickly absorbing the composition into the skin. This dry absorbable emollient oil is generally not greasy, a desirable attribute. However, this attribute can be unpleasant if the dry absorbable oil is the only oil in the oil phase. Because such an oil is easily absorbed, it leaves no positive "feel" on the skin. Therefore, it should be balanced with one or more substantive skin conditioning oils or waxes, which are soothing and coat the skin, leaving an "afterfeel" perceptible to the user. These substantive oils and waxes have these desirable traits, but, when used in excess, can leave a greasy feeling on the skin. Thus, the benefit of the emulsion base of this invention is that it balances the esthetics of the compositions with respect to the oil phase and has the capability of rebalancing it with respect to other ingredients which may provide active skin conditioning and/or therapeutic benefits. Preferably, the ratio of dry absorbable emollient oil to substantive skin conditioning oils is from about 1:3 to about 10:1. More preferably, the ratio is from about 1:3 to about 5:1. Most preferably, the ratio should be about 1:1. The dry absorbable emollient is most preferably C12–15 alkyl benzoate (commercially available as Finsolv TN from Finetex), capric-caprylic triglycerides (commercially available from Huls as Miglyol 812) or other suitable synthetic triglycerides known to those of skill in the art. Substantive oils or waxes may be selected from white petrolatum, octyl hydroxystearate, cetyl palmitate and the like. The total amount of oil phase may vary from a very low level, e.g., about 2% of the overall composition, to as much as about 20% of the composition. More preferably, the oil phase should be composed of from about 5 to about 12% of the composition in order to provide the desired spreadability and consistency without leaving excessive residue with the perception of greasiness and oily coating on the skin. Variations within this range may depend upon the characteristics of the additional components, including vitamins, sunscreens and the like, both to serve as a vehicle to apply the active ingredients properly to the skin and to modify the sometimes undesirable esthetics contributions from these components.

In addition to such oils, other emollients and surface active agents have been incorporated in the emulsions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/ dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

It is also preferable to have at least one oil-soluble antioxidant in the compositions of this invention. The oil-soluble antioxidants which are useful in the compositions of the present invention include butylated hydroxytoluene (BHT), ascorbyl palmitate, butylated hydroxyanisole (BHA), phenyl-a-naphthylamine, hydroquinone, propyl gallate, nordihydroguaiaretic acid, rosemary extract and mixtures thereof as well as any other known oil-soluble antioxidant compatible with the other components of the compositions.

Preferably, a water-soluble antioxidant should be present in the water phase of the compositions of this invention. The water-soluble antioxidants which are useful in the compositions of this invention include ascorbic acid, sodium metabisulfite, sodium bisulfite, sodium thiosulfite, sodium formaldehyde sulfoxylate, isoascorbic acid, thioglyerol, thiosorbitol, thiourea, thioglycolic acid, cysteine hydrochloride, 1,4-diazobicyclo-(2,2,2)-octane, malic acid, fumaric acid, licopene and mixtures thereof as well as any other known water-soluble antioxidant compatible with the other components of the compositions.

The composition of this invention can contain additives, as required, such as a humectant, an antioxidant, a preservative, a flavor, fragrances, a surface active agent, a binder, and the like, as well as skin protectant agents, therapeutic agents and "cosmeceuticals".

Preferably, a detackifying material should be incorporated into the compositions of this invention. When emulsions are applied to the skin, they break apart. Often, they leave a sticky feeling as they dry before the emulsion has totally broken and been absorbed into the skin. This is particularly true of emulsions containing cetyl and stearyl alcohols, due to the liquid crystal nature of these materials, as they are quite slow to give up water upon application to the skin. Unexpectedly, it has been found that certain detackifying materials may be added to the compositions of this invention in order to combat this stickiness. Materials having a "talc-like" character, i.e., which crystallize into a plate-like form, are preferable for use as they add lubricity to the compositions of this invention. Other non-platey solids, although less preferably, are also acceptable for use as a detackifier. Preferably, the detackifying material used in the compositions of this invention should be lauroyl lysine, titanium dioxide, zinc oxide, pulverized nylon, oatmeal and surface treated oatmeal, silica, mica, barium sulfate, aluminum starch, octenyl succinate, micronized polyethylene, boron nitride, corn starch, talc or silicone waxes or oils and other insoluble particles which do not leave visual residue on the skin. More preferably, the detackifying material should be lauroyl lysine, boron nitride, mica and talc. Most preferably, the detackifier should be lauroyl lysine (such as Amihope LL commercially available from Ajinomoto). Preferably, the detackifier is present at very low concentrations, i.e., from about 0.01 to about 7% by weight. More preferably, it should be present at the amount of from about 0.5 to about 1% by weight. Other detackifying materials which are compatible with fatty emulsions would also be appropriate for use in the compositions of this invention.

Surprisingly, it has also been found that small concentrations of lower alkyl alcohols also contribute an esthetically benefit to the compositions of this invention. It has been found that the addition of lower alkyl solvent alcohols mitigate the waxy feel of the emulsions on the skin due to the presence of cetyl and stearyl alcohols. It is believed that lower alkyl alcohols assist in solubilizing the liquid crystal structures formed by these fatty alcohols. Preferably, lower alkyl alcohols having from one to four carbon atoms are useful in the compositions of this invention. Most preferably, ethyl alcohol should be present in the compositions of this invention. Preferably, they should be present in an amount of from about 2 to about 10% by weight of the compositions.

Examples of the humectant include glycerol, sorbitol, propylene glycol, ethylene glycol, 1,3-butylene glycol, polypropylene glycol, xylitol, maltitol, lactitol and the like. They may be used either singly or in combination.

Examples of the preservatives include salicylic acid, chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate and the like.

Examples of the flavor and fragrance include menthol, anethole, carvone, eugenol, limonene, ocimene, n-decylalcohol, citronellol, a-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, eucalyptus oil and the like.

Examples of surface active agents include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium a-olefin sulfonate and sodium dioctylsulfosuccinate; N-alkylaminoglycerols, e.g., N-lauryldiaminoethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate. Emulsifier-type surfactants known to those of skill in the art should be used in the compositions of this invention.

Examples of the binder or thickener include cellulose derivatives such as alkali metal salts of carboxymethylcellulose, methyl cellulose, hydroxyethyl cellulose and sodium carboxymethylhydroxyethyl cellulose, alkali metal alginates such as sodium alginate, propylene glycol alginate, gums such as carrageenan, xanthan gum, tragacanth gum, caraya gum and gum arabic, and synthetic binders such as polyvinyl alcohol, polysodium acrylate and polyvinyl pyrrolidone. Thickeners such as natural gums and synthetic polymers, as well as preservatives such as methylparaben, butyl paraben, propylparaben and phenoxyethanol, coloring agents and fragrances also are commonly included in such compositions.

The antioxidants should be utilized in a stabilizing effective amount and may range in total from about 0.001 to 5% based on the weight of the total composition, preferably from about 0.01 to about 1%. The amount of antioxidants utilized in the compositions of the present invention is dependent in part on the specific antioxidants selected, the amount of and specific retinoid being protected and the processing conditions.

In certain aspects of this invention, the compositions should include a chelating agent. The retinoid compounds of this invention are sensitive to metal ions and in particular to bi- and tri-valent cations and in certain instances, appear to degrade rapidly in their presence. The chelating agent forms a complex with the metal ions thereby inactivating them and preventing them from affecting the retinoid compounds. Chelating agents which are useful in the compositions of the present invention include ethylenediamine tetra acetic acid (EDTA) and derivatives and salts thereof, dihydroxyethyl glycine, citric acid, tartaric acid, and mixtures thereof. The chelating agents should be utilized in a stabilizing effective amount and may range from about 0.01 to about 2% based on the weight of the total composition, preferably from about 0.05 to about 1%. Most preferably, the chelating agent should be EDTA.

The retinoid compounds which are useful in the compositions of the present invention consist of Vitamin A alcohol (retinol), Vitamin A aldehyde (retinal) and Vitamin A esters (retinyl acetate and retinyl palmitate), although other retinoids may be incorporated into the emulsion compositions of this invention. These retinoids are utilized in the compositions of the present invention in a therapeutically effective amount that may range from about 0.001 to about 5% by weight of the total compositions, preferably from about 0.001 to about 1%.

Other active ingredients such as sunscreen materials and antimicrobial materials may be utilized in the compositions of the present invention provided that they are physically and chemically compatible with the other components of the compositions. For example, moisturizing agents such as propylene glycol, allantoin, acetamine MEA, oat protein and hyaluronic acid and other humectants may be added to the retinoid-containing formulations of this invention in order to provide moisturizing activity in conjunction with the retinoid-related activity of the products. Other proteins and amino acids may also be incorporated. Sunscreens may include organic or inorganic sunscreens, such as octylmethoxycinnamate and other cinnamate compounds, titanium dioxide and zinc oxide and the like.

Various irritancy mitigants may be added to the compositions of this invention. Retinoid-containing compositions tend to irritate the skin, therefore irritancy mitigants assist in preventing undue discomfort to the user, while potentially permitting the dosage level of retinoid to be increased, thereby making the product more effective. Irritancy mitigants such as a-bisabolol, panthenol, green tea extract, allantoin, ginkgo biloba, stearoyl glycyrrhetinic acid (licorice extract), tea tree oil, butchers' broom, calendula, ginseng and the like may be added.

It has also been found, surprisingly, that certain materials provide a mitigation of irritation due to retinoids which have not previously evidenced or would have been expected to evidence such activity. For example, retinoid-containing compositions which also contain octylmethoxycinnamate had very low irritation on the skin when compared with identical compositions which did not contain octylmethoxycinnamate. Generally, it has been found that certain compounds afford lower irritation in formulations containing similar levels of retinoid than formulations which do not contain such irritation-mitigation agents.

It has been observed that compounds having similar solubility attributes to those of retinoid compounds tend to mitigate irritation caused by such compounds (hereinafter, "irritation mitigation agents"). Solubility attributes of two or more materials with respect to each other are generally reflected in the "solubility parameter", $\delta$, which is expressed in the units $(cal/cm^3)^{1/2}$. It is believed that the presence of the irritation mitigation agents having similar solubility properties to those of retinoid compounds tend to assist in solubilizing the retinoids in the oil phase. Due to the fact that retinoids tend to be oil-soluble, the irritation mitigation agents of this invention should also preferably be oil-soluble such that the irritation mitigation agents and retinoids are present in the same, oil phase. The irritation mitigation agents, it is believed, thereby act within the oil phase to maintain the retinoids in that phase and delay and/or modulate their release to the skin upon topical application. The retinoids therefore tend to be delivered to the skin in a more even dose rather than as a "bolus" in a high dose. This modulation in delivery to the skin is the most likely cause of the decreased irritation.

It is believed that irritation mitigation agents having a solubility parameter δ close to that of the retinoid compounds utilized in the compositions of this invention will modulate delivery to the skin and consequently decrease irritation engendered by the retinoids. The value of the solubility parameter can be estimated from tabulated molecular substituent constants such as those described by Fedors. These substituent constants can be found in *Solubility and Related Properties* by Kenneth C. James, pp. 185–187, Marcel Dekker, Inc. (1986). Generally, according to *Textbook of Polymer Science*, 2nd Ed., Billmeyer, solubility can be expected if the difference of the solubility parameters of two materials is less than about 2 units. More preferably, the difference of the solubility parameters should be less than 1.5 units and, more preferably, less than 1 unit.

One or more irritation mitigation agents may be useful in effecting irritation mitigation in a given composition according to this invention. In effect, the oil phase can be regarded as providing irritation migitating effects dependent upon the solubility attributes of the phase and/or its components. Furthermore, a combination of materials which alone might not be effective may be useful in mitigating irritation, depending upon the solubility parameter of the combination. The solubility of a blend of materials may be found according to the following formula:

$$\delta_{blend} = \Sigma_{1-n}\{(\delta_1 \times V_1) + (\delta_2 \times V_2) + \ldots + (\delta_n + V_n)\}$$

where V represents the volume fraction of the particular material in the composition (See Kirk-Othmer Encyclopedia of Chemical Technology, 3rd Ed.).

Preferably, the irritation mitigation agents of this invention are oil-soluble compounds, more preferably, organic ester compounds. More preferably, oil-soluble organic ester compounds having a solubility parameter within 2 units of that of a retinoid compound should be useful in mitigating retinoid irritation. For example, the irritation mitigation agents may be selected from esters of fatty acids and/or esters of fatty alcohols. Most preferably, the oil-soluble organic ester compounds are selected from the following group: $C_{12-15}$ Alkyl benzoate, octyl methoxycinnamate, octocrylene, menthyl anthranilate, homomenthyl salicylate, glyceryl stearate, PEG 100 stearate, and stearyl lactate or a mixture thereof. Effective compounds may also be selected from the following: octyl dimethyl PABA, cetyl alcohol, stearyl alcohol, and the like, i.e., organic compounds having a carbon chain having from about 12 to about 18 carbon atoms and an appropriate solubility parameter.

Preferably, the irritation mitigation agent (such as octyl methoxycinnamate) should be present in an amount from about 3 to about 12 weight percent of the formulation. More preferably, the irritation mitigation agent should be present in an amount from about 3 to about 6 weight percent of the composition.

It is believed that such organic esters may control retinoid delivery in that they may solubilize or associate with the retinoid. Alternatively, hydrolysis of these esters may produce aromatic carboxylic acids, which may act as weak anti-inflammatory agents.

Other ingredients may include agents which assist in protecting the skin from aging, such as sunscreens, anti-oxidant vitamins such as ascorbic acid, vitamin B, biotin, pantothenic acid, vitamin D, vitamin E and vitamin C. Yeast extract, gingko biloba, bisabolol, panthenol, alpha hydroxy acids and oligosaccharides such as melibiose are among other ingredients which assist in preventing aging of the skin by such means as irritation mitigation, oxidation mitigation, healing, affecting retinoid metabolism and inhibiting the production of elastase.

Skin color evening ingredients and depigmentation agents may also be effective in the products of this invention. Such ingredients may include hydroquinone, licorice extract, kojic acid, gatuline A (pilewort extract), micromerol (butylene glycol and apple extract), glutathione, arbutin, placenta extract, ascorbic acid, magnesium-L-ascorbyl-2-phosphate and the like.

Compositions which assist in the reduction of lines and wrinkles may also be added to the compositions of this invention. For example, alpha hydroxy acids, hyaluronic acid, Gatuline R (fagus silvitica extract), pigments and scattering aids such as mica, zinc oxide and titanium dioxide may be used in the compositions of this invention in this capacity. Various natural extracts such as tannins, fiavenoids, saponins and the like may also be added.

Anti-inflammatory agents may also be used in the compositions of this invention. Not only should these agents assist in mitigating irritation, they may assist the retinoids in treating wrinkles and lines in the skin. Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxycorticosterone acetate, dexamethasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone and mixtures thereof may be used. Preferably, hydrocortisone may be used.

Nonsteroidal anti-inflammatory agents may also be employed in the compositions of this invention, such as salicylates (including alkyl and aryl esters of salicylic acid), acetic acid derivatives (including arylacetic acid and its derivatives), fenamates, propionic acid derivatives and pyrazoles or mixtures thereof. Other synthetic and natural anti-inflammatory agents may also be used.

Additional active ingredients having topical activity may be utilized in the compositions of this invention. Azole-type anti-fungal and anti-bacterial agents may be employed in the compositions of this invention in their base form. For example, ketoconazole, miconazole, itraconazole, metronidazole, elubiol, and like related imidazole antifungals and antibacterials are useful in the topical formulations of this invention.

The compositions of the present invention can be prepared by well-known mixing or blending procedures. Each phase of the emulsion is preferably separately prepared with all of the components contained in the appropriate phase, except that it is usually preferred to omit the retinoid compound initially. The emulsion is then formed normally by adding the oil phase to the water phase with agitation. Preferably, the water phase should be added into the oil phase, as it results in increased stability. It is preferred that the portions be prepared under oxygen-depleted atmosphere such as a nitrogen or argon gas blanket. Most preferably, argon or nitrogen gas is bubbled through the water phase prior to phasing in the oil phase. Commercially, it is envisioned that such oxygen depleted atmosphere may be obtained by operating under vacuum conditions and that the product be stored, prior to use, in blind-end containers, preferably aluminum tubes.

This invention relates not only to stable and esthetic retinoid-containing compositions used in skin care, and to methods of making such compositions, it also relates to an apparatus and method of storing such compositions prior to use. Previously, numerous products containing retinol or its esters or aldehyde have been marketed in packages which follow the convention for personal care products in being composed of principally low or high density polyethylene or polypropylene usually containing a pigmenting substance included within the package resin. Although this package technology is ordinarily suitable for toiletries, it has been found that these package materials are not satisfactory for retinoid materials, particularly retinol and retinal, as they transmit sufficient light combined with sufficient oxygen to lead to degradation of the vitamin substance into foreign materials not ordinarily found in mammalian metabolism, such as a variety of cis-isomers of the polyene moiety of the retinoid side chain, as well as oxidative degradation products and hydrolysis products. It has been found that a combination of proper manufacturing procedures as described can provide the fresh product in suitable form to the consumer, but over time, without exclusion of the destabilizing influences of light and oxygen, the foreign degradative substances accumulate, reducing the extent of the desirable attributes of the product.

In some cases, such as the retinaldehyde-containing product "Ystheal", commercially available from Pierre Fabre of France, a package structure which minimizes the tendency of the package to inhale air after dispensing product has been used, thus minimizing the exposure of product to oxygen. However, since the package is made of pigmented polypropylene, it is not sufficiently protective of light intrusion into the product. Many package forms, such as plastic tubes, bottles, or jars, are ineffective in protecting product from either air or light.

The skin care composition should neither be directly contacted with oxygen or an oxygen-containing gas such as air, nor contacted with oxygen passing through the wall of the container. Portions in contact with the outside, which constitute the container, such as a wall, an opening, etc. of the container, are required to have excellent oxygen barrier properties. The container must also be designed not to pass oxygen when feeding the skin care composition to the container or when removing the composition from the container.

If has been found that sufficient exclusion of these destructive influences may be obtained only by use of packages constructed in part of aluminum, which is totally opaque to light and totally excludes oxygen permeation of the package walls. Additionally, given that the aluminum is not elastic, unlike plastic tubing, it has minimal tendency to suck back air after dispensing product. Another package structure which is adequate to protect retinoid-containing products is that constructed with plastic film laminates including a layer of aluminum foil. The aluminum foil provides the protection of the aluminum tube, while the plastic film layers permit more conventional package esthetics. Another construction which is highly desirable for retinoid product protection is one which is constructed of aluminum foil or aluminum plastic laminate films of thin gauge and of broad and thin dimensions, sufficient so that the package can collapse as product is withdrawn, preventing air inhalation after product is dispensed. Such foil structures may be contained within a physically protective and esthetic oversleeve of conventional plastic, enabling safe shipping and handling during processing, as well as when it reaches consumers.

It has also been found that by using a pouch-type container in which a composition is out of contact with oxygen, the composition can be used as not only a water-in-oil type emulsion but also an oil-in-water type emulsion. Further, even after use is begun, the contact with oxygen can be blocked, making it possible to substantially prevent decomposition or degradation of the retinoid in the skin care composition.

More specifically, this invention relates to a container in which the skin care composition is out of contact with oxygen in a two-compartment container such as a pouch-type container, further to a skin care composition which is stored in a two-compartment container which are made of films. Preferably, the film materials of the inner container are formed from a monolayer film or multilayer film. The film materials are preferably selected from the following materials: aluminum and AAS and ethylene-vinyl alcohol copolymer. More preferably, the pouch-type container contains film materials which are laminated in the following order, beginning from the innermost portion of the film: polyethylene terephthalate, nylon, aluminum and an AAS resin or polypropylene. Further, this invention relates to a skin care composition which is stored in a container having an aerosol-system using a liquefied gas or a compressed gas.

If such a requirement is satisfied, the shape of the container in which the composition is out of contact with oxygen is not particularly limited in this invention, and can be a tube, a pump dispenser, a compressed dispenser, a bottle, a spray, a sachet or the like. From the aspects of production, treatment and an oxygen-barrier type, the two-compartment container is preferred and, the pouch-type container is especially preferred. Such a two-compartment container generally means a container consisting of an outer container and an inner container which is accommodated in the outer container and stores the content therein, but is not particularly restricted if the container can store and isolate the content from outside. A "pouch-type container" means a container having an outer container and a pouch which is accommodated in the outer container, is provided with a valve which stores the contents therein.

This pouch is a bag-like container whose wall is formed of a film and which is provided with an opening through which to pass the contents. The two-part container actually used is preferably an aerosol-system. The aerosol-system here referred to is a system in which the inside of the container is kept in a state pressurized with a propellant, and the content is sprayed with the propellant by opening a valve, or a system in which the content is discharged outside the container with the pressure of the propellant.

A liquefied gas or a compressed gas is used as a propellant. Examples of the liquefied gas include chlorofluorocarbons, dimethyl ether, liquefied petroleum gas (LPG) and chlorinated hydrocarbons. Examples of the compressed gas include a nitrogen gas, a carbon dioxide gas, a nitrous oxide ($N_2O$) and argon. The liquefied gasses are preferable when considering a uniformity of discharge amount of the content, and the compressed gasses are preferable in minimizing interaction with the content, influence on the human body and the like.

An ordinary aerosol is generally formed by charging a stock solution and propellant in a container and sealing the container with a valve. In a general filling method, the content is charged into the container from an opening, and after the opening is sealed with a valve the propellant is further charged. According to such an ordinary filling method, however, it is quite difficult to prevent the contact between the content such as a lotion or the like and oxygen. There is further a problem that the content is directly contacted with the propellant within the pouch by being partially mixed therewith. Taking into account the problem of stability of the retinoid compound, the container of the ordinary aerosol-system in which the content is mixed with the propellant cannot be used in the skin care composition of this invention.

Accordingly, the two-part container in this invention, unlike the ordinary container, consists of an outer container and a pouch having a valve. Only the content (skin care composition) is contained in the inner container and the propellant is not; along with the inner container, the propellant is stored in the outer container. Similarly the pouch-type container of this invention consists of an outer container and a pouch having a valve. Only the skin care composition is contained in the pouch and the propellant is not; along with the pouch, the propellant is stored in the outer container. Employment of such a method prevents the contact between the skin care composition and the propellant, thereby making it possible to prevent decomposition or degradation of the retinoid in the skin care composition.

A method of filling the contents in the inner container is not particularly limited and methods such that the oxygen does not invade the inner container and not contact the contents may be applicable, as known to those of ordinary skill in the art. Preferably, the contact between oxygen and the skin care composition of this invention should be performed such that filling takes place in an atmosphere of inert gas such as nitrogen or argon. The content is filled in the pouch as follows. First, the pouch and propellant are placed within the outer container and said outer container is then sealed with the valve. In this state, a gas within the pouch is expelled with the pressure of the propellant so that the inside of the pouch is almost completely degassed. After that, the content is filled in the pouch under pressure. The content is, when filled by this method, scarcely contacted with oxygen in the filling. Preferably, if the content is filled in inert gas such as nitrogen or argon, the contact with oxygen is more completely blocked.

Further, even after the content is filled, it is double partitioned from the open air by an oxygen-impermeable film used in the pouch and the outer container, and the contact between oxygen in an ambient atmosphere and the skin care composition within the pouch is completely prevented.

The conventional tube-type container is completely sealed before first opened. However, once it is opened and started to be used, entrance of oxygen is permitted whenever it is opened for use, though the contact with air is prevented with a cap during storage. Meanwhile, when the two-part container is used, oxygen does not enter even after starting to use it.

The material of the container of this invention in which the composition is out of contact with oxygen is not particularly limited. However, a multilayered film constituting the inner container in the two-compartment container is preferable, from the aspects of sealing retention, oxygen-barrier properties and stability to the skin care composition. More preferable is a multilayered film composed of at least two kinds selected from the group consisting of polyethylene terephthalate, nylon, aluminum, polypropylene, an AAS resin and an ethylene/vinyl alcohol copolymer. Especially preferable are a multilayered film obtained by laminating polyethylene terephthalate, nylon, aluminum and the AAS resin in this order as film materials from the innermost layer to the outermost layer of the pouch, and a multilayered film obtained by laminating polyethylene terephthalate, nylon, aluminum and polypropylene in this order as materials from the innermost layer to the outermost layer.

Polyethylene terephthalate is a polyester resin having a chemical structure obtained by polycondensing terephthalic acid with ethylene glycol. Nylon includes various polyamide resins. The AAS resin is a resinous polymer formed by graft polymerizing acrylonitrile as a main component with copolymer components including an acrylate ester and butadiene, and can be obtained, for example, under a trade name "BAREX" from Mitsui Toatsu Chemicals, Inc.

The ethylene/vinyl alcohol copolymer is a resinous polymer produced by saponifying a random copolymer of ethylene and vinyl acetate, and be obtained, for example, under a trade name "EVAL" from Kuraray Co., Ltd.

The two-part container of this invention can be used, as is apparent from the foregoing explanation, in not only the retinoid-containing skin care composition but also liquid substances of various forms, e.g., an emulsion, a suspension, an aqueous solution and an oil. Especially, it is suitable for storage of substances required to protect the content from an external environment such as air.

Figure 1A:
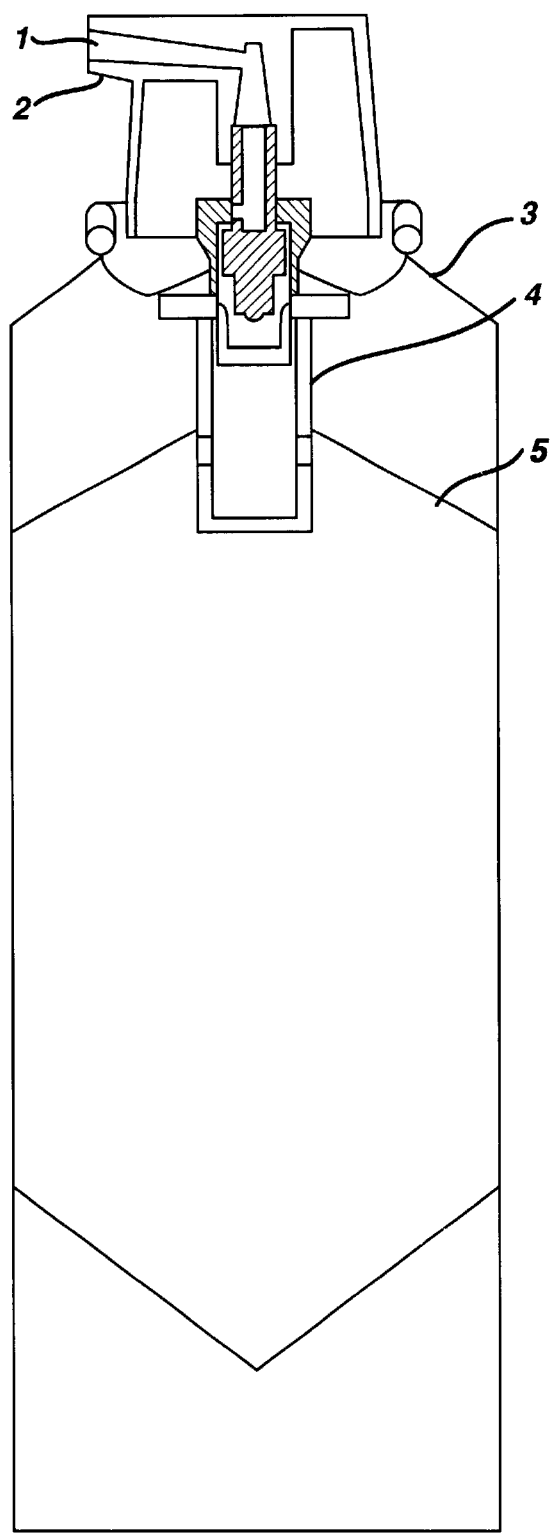
FIG. 1 is a front view of an example of an example of an outer container in which the pouch of this invention is placed. When a cap is pushed down, a skin care composition is injected from an opening of a valve.
Figure 1B:
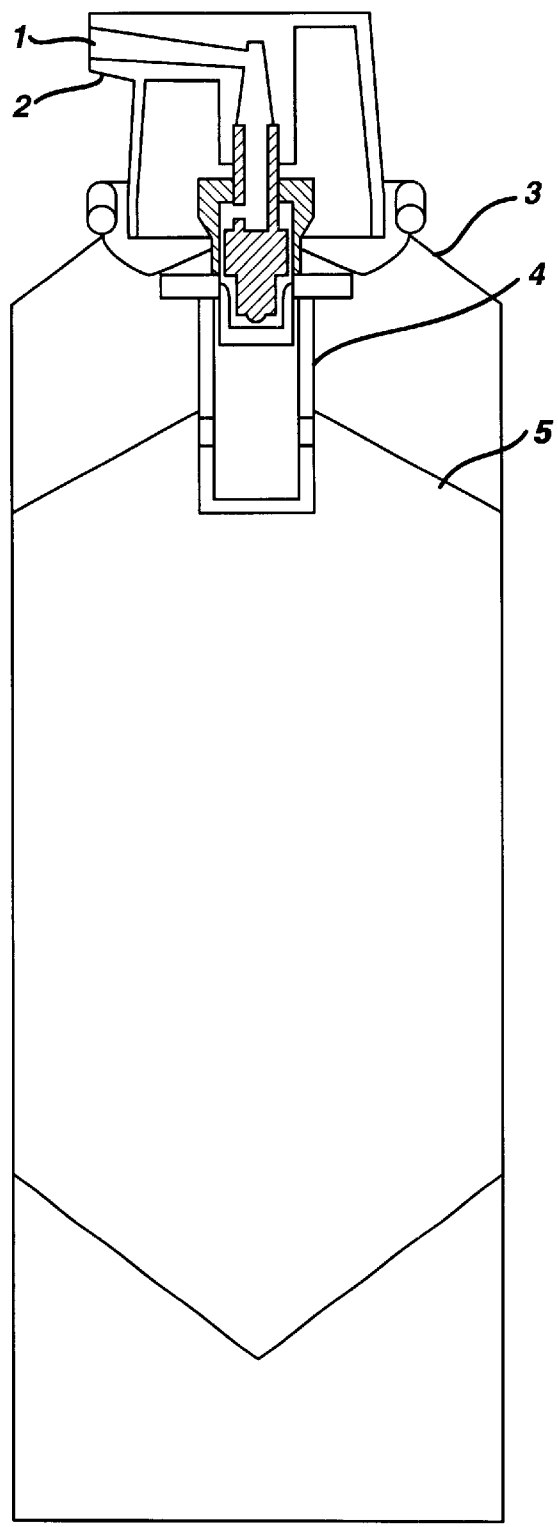
Figure 2:
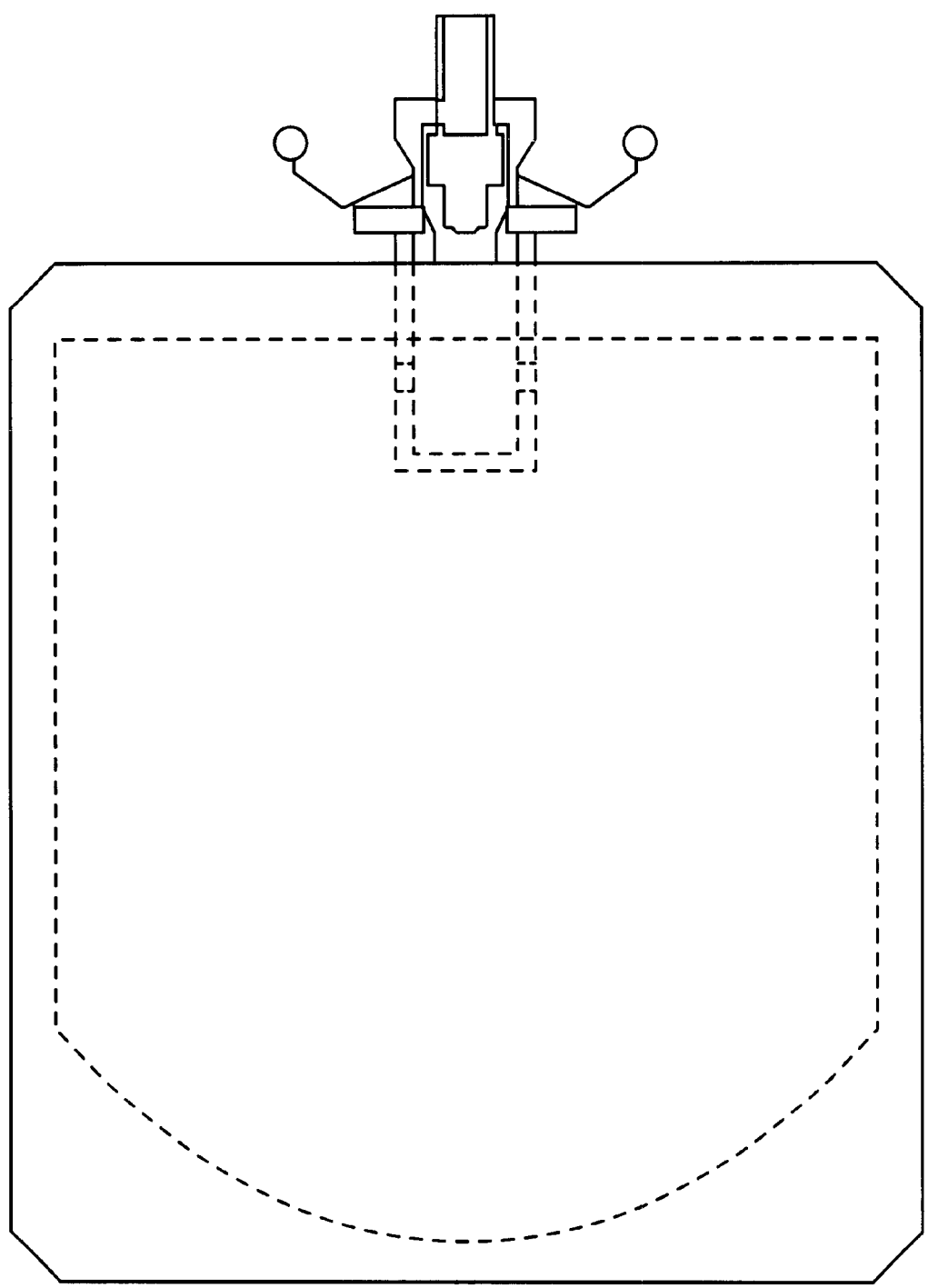
FIG. 2 is a front view of the pouch in this invention.
Figure 3:
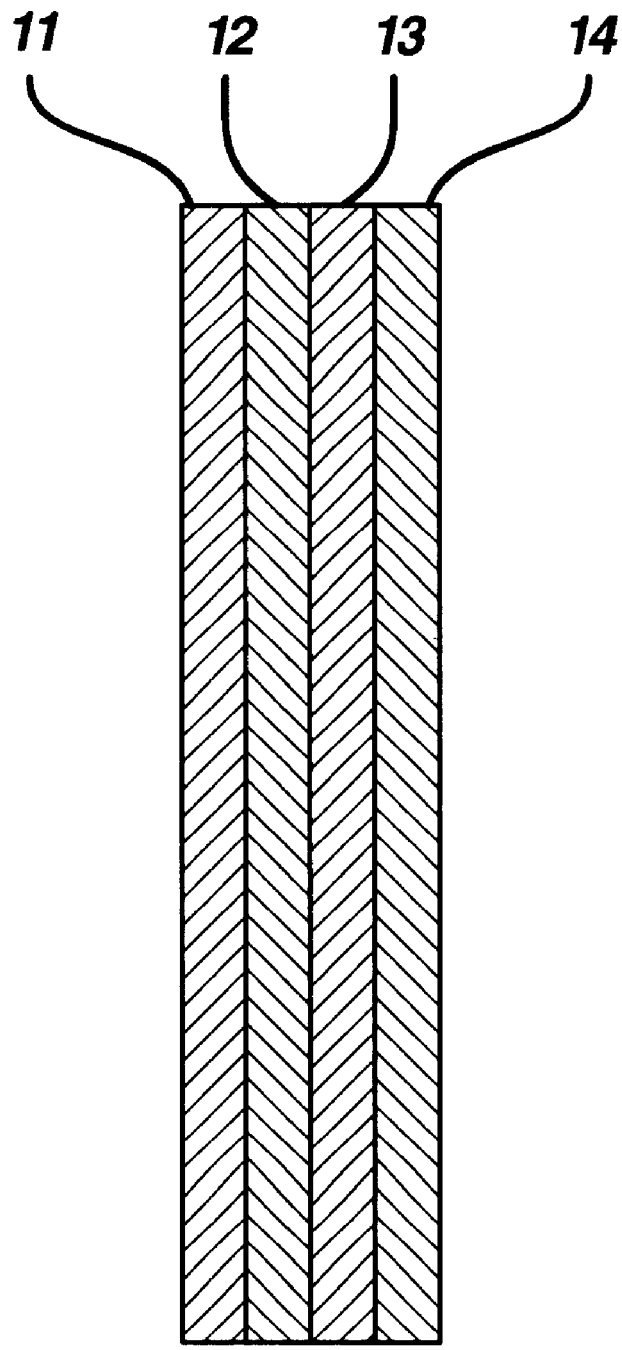
FIG. 3 is a sectional view of a multilayered film used in the pouch.

The advantages of the invention and specific embodiments of the skin care compositions prepared in accordance with the present invention are illustrated by the following examples. It will be understood, however, that the invention is not confined to the specific limitations set forth in the individual examples, but rather to the scope of the appended claims.

EXAMPLE 1

The formulations of this Example 1 were prepared by first creating the water phase and then creating the oil phase. After both phases were created, they were mixed together and retinol added. The water phase was made by first weighing deionized water into a beaker and, with mixing at high speed, slowly adding carboxy polymer (carbomer). The mixture was then stirred for a few minutes. EDTA and ascorbic acid were added to the mixture and mixing was continued for forty-five minutes or until well-dissolved. The water phase was then heated to 80° C., at which time propylene glycol was added. To make the oil phase, all ingredients of the oil phase were weighed and added together in a separate beaker. The oil phase was then heated to 80° C. with mixing until homogeneous. The oil phase was then slowly phased into the water phase with mixing. After phasing, the emulsion was apportioned into four parts and sodium hydroxide was added at 80° C. to each portion separately in order to adjust the pH of the emulsion. The portions were adjusted to have pH of 4.5, 6.0, 7.0 and 9.0, respectively. After mixing for ten minutes, the emulsion was cooled to 45° C. Retinol 40% was then added to the emulsions and the emulsions mixed until homogeneous. The procedure was carried out under yellow light and under an argon blanket so as to minimize exposure to oxygen. Retinol concentrations were measured in accordance with the general HPLC procedure set forth below in Example 2, however, a different column was used containing a mobile phase of 65% acetonitrile, 35% phosphate buffer and a C18 column and a UV detector at 325 nm.

The components of the formulations of this example were as follows:

| Components | Content | (% W/W) |
|---|---|---|
| Carboxyvinyl polymer | 0.300 | |
| Propylene glycol | 5.00 | |
| Methylparaben | | 0.15 |
| Ascorbic Acid | | 0.10 |
| Glyceryl monostearate & PEG 100 Stearate | 5.00 | |
| Cetanol (cetyl alcohol) | 1.00 | |
| Stearyl alcohol | 0.50 | |
| White Petrolatum | 1.50 | |
| BHT | 0.05 | |
| Propylparaben | | 0.10 |
| Butylparaben | | 0.05 |
| Cetyl palmitate | 1.00 | |
| C12–C15 Alkyl Benzoate | 4.00 | |
| Benzyl alcohol | | 0.30 |
| Ethyl alcohol | | 4.00 |
| Disodium EDTA | 0.05 | |
| Retinol 40% | 0.366 | |
| Sodium Hydroxide (10%) | to adjust pH | |
| Water | q.s. | |

The four emulsions were again apportioned into two parts each, and one of each part held at 50° C., the other part held at 40° C. The stability of all four emulsions was measured over a period of eight weeks. The stability data is set forth below in Table 1.

TABLE 1

| Weeks | Temperature | pH | % Retinol From Initial |
|---|---|---|---|
| 2 | 50° C. | 4.5 | 80.19 |
| | | 6.0 | 93.67 |
| | | 7.0 | 97.07 |
| | | 9.0 | 96.01 |
| 4 | 40° C. | 4.5 | 82.65 |
| | | 6.0 | 95.72 |
| | | 7.0 | 97.64 |
| | | 9.0 | 95.77 |
| | 50° C. | 4.5 | 64.35 |
| | | 6.0 | 94.43 |
| | | 7.0 | 95.92 |
| | | 9.0 | 94.74 |
| 8 | 40° C. | 4.5 | 74.98 |
| | | 6.0 | 94.48 |
| | | 7.0 | 96.24 |
| | | 9.0 | 94.76 |
| | 50° C. | 4.5 | 45.13 |
| | | 6.0 | 90.99 |
| | | 7.0 | 94.33 |
| | | 9.0 | 89.68 |

Thus, it can be seen that, although acceptable stabilities can be achieved at pH about 4.5, higher pH yields increased stability in the formulations of this invention.

EXAMPLE 1A

An oil-in-water emulsion was prepared in accordance with the procedure set forth in Example 1, using the components set forth below. Again, the emulsion was divided into four parts and the pH adjusted, this time to 4.5, 6.0, 8.0 and 10.0. Each part was further divided into two portions, one being held at 40° C. and one held at 50° C. for a period of seven weeks.

The results of the stability measurement are set forth in Table 1A below. Again, it can be seen that, as the pH increased, the stability increased.

| Components | Content | (% W/W) |
|---|---|---|
| Disodium EDTA | 0.10 | |
| Ascorbic Acid | 0.10 | |
| Methylparaben | 0.15 | |
| Mineral Oil | 8.00 | |
| Stearyl Alcohol | 1.00 | |
| BRIJ 721 (Steareth 21) | 2.00 | |
| BRIJ 72 (Steareth-2) | 2.00 | |
| BHT | 0.05 | |
| Propylparaben | | 0.10 |
| Retinol 40% | 0.366 | |
| Deionized Water | Q.S. | |
| Sodium Hydroxide 10% | to adjust pH | |

TABLE 1A

| Weeks | Temperature | pH | % Retinol From Initial |
|---|---|---|---|
| 2 | 50° C. | 4.5 | 87.87 |
| | | 6.0 | 95.63 |
| | | 8.0 | 98.37 |
| | | 10.0 | 96.95 |
| 7 | 40° C. | 4.5 | 89.4 |
| | | 6.0 | 94.0 |
| | | 8.0 | 95.4 |
| | | 10.0 | 96.3 |
| | 50° C. | 4.5 | 75.0 |
| | | 6.0 | 89.2 |
| | | 8.0 | 91.5 |
| | | 10.0 | 94.5 |

EXAMPLE 2

As a skin care composition containing a retinoid, an oil-in-water type lotion having the formulation shown in Table 2 was prepared in accordance with the procedure set forth in Example 1. As the retinoid, retinol was used. Concentrations of retinol and other retinoids such as retinal (vitamin A aldehyde), retinyl acetate and retinyl palmitate can be determined by any suitable analytical procedure.

TABLE 2

| Components | Content (% by Weight) |
|---|---|
| Carboxyvinyl polymer | 0.1 |
| Propylene glycol | 5.0 |
| Methylparaben | 0.15 |
| Sodium hydroxide | 0.041 |
| Ascorbic acid | 0.1 |
| Glyceryl monostearate & PEG 100 Stearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |

TABLE 2-continued

| Components | Content (% by Weight) |
|---|---|
| Higher alcohol benzoic acid ester | 4.0 |
| Benzyl alcohol | 0.3 |
| Ethyl alcohol | 5.0 |
| Disodium edetate | 0.05 |
| Retinol | 0.075 |
| Purified water | q.s. |
| Total | 100 |

A storage test was performed using three pouch-type aerosol containers of this invention which consisted of a pouch and contained LPG as a propellant correspondingly to the three test temperatures shown in Table 3. The pouch of said aerosol container was produced with a four-layered film obtained by laminating polyethylene terephthalate, nylon, aluminum and an AAS resin in this order as film materials from the innermost layer to the outermost layer. The above skin care composition was distributed in each of the three containers to form three samples. The method of distribution of the skin care composition is as follows. First, the pouch is placed in the outer container and LPG is charged in the outer container and outside of the pouch and sealed, thereby a gas in the pouch is expelled with the pressure of the LPG. In this state, the skin care composition is filled in the pouch under pressure. The three samples were allowed to stand in a constant temperature chamber adjusted to 40° C.±1° C., a constant temperature chamber adjusted to 4° C.±1° C. and at room temperature. Samples for analysis were collected from the same samples through an injection nozzle with the pressure of the propellant before the start of the test, 4 weeks later, 8 weeks later and 13 weeks later. One gram of each sample for analysis was accurately weighed and collected. A retinoid was extracted with an ethyl acetate/methanol mixed solution, and an amount of the retinoid was determined by a light absorption analysis at a wave length of 325 nm using a liquid chromatograph. As reported herein, we determined retinoid concentrations by a high performance liquid chromatography (HPLC) procedure in which the chromatograph was equipped with a reversed phase 5 micron C-8 column (25 cm in length×4.6 mm in diameter) and a UV detector at 340 nm. The sample to be analyzed was diluted with a solution of 50% by weight methanol and 50% by weight ethyl acetate to a concentration of 18 micrograms/ml and the retinoid was detected at 340 nm. The gradient mobile phase consisted of an organic portion composed of 5 percent tetrahydrofuran in acetonitrile and an aqueous portion consisting of 0.05N ammonium acetate. The solvent program has an initial composition of 70% organic/30% aqueous which increases linearly to 80%, organic/20% aqueous at 3 minutes, then again increases linearly to 100% organic at 15 minutes, where it stays until 19 minutes. After injecting 15 microliters of sample solution into the chromatograph, the analytical conditions were run at a flow rate of 2 ml/min and thermostatically regulated at 40° C. The retention time of retinol (Vitamin A alcohol) is about 6.4 minutes. The retention times of retinal (vitamin A aldehyde), retinyl acetate, and retinyl palmitate are about 7.5 mins., 10.1 mins. and 18.7 mins., respectively. The HPLC results were found to be reproducible to better than a 3% range of standard deviation. The results are shown in Table 3 below.

EXAMPLE 3

The storage test was performed to determine the amount of a retinoid in the same manner as in Example 2 except that a pouch was used which was produced with a four-layered film obtained by laminating polyethylene terephthalate, nylon, aluminum and polypropylene in this order as materials form the innermost layer to the outermost layer, that a nitrogen gas was used as a propellant and that the distribution of the skin care composition is performed by the following method, a pouch is placed in an outer container then the skin care composition is filled in the pouch, the pouch is sealed with a valve, a nitrogen gas is charged inside the outer container and outside the pouch and sealed. The results are shown in Table 3.

COMPARATIVE EXAMPLES 1 AND 2

The storage test was performed to determine the amount of a retinoid in the same manner as in Example 1 at the temperature listed in Table 3 below, except using a sealed aluminum tube in Comparative Example 1, an aerosol container not using a pouch in Comparative Example 2. The results are shown in Table 3. When an aluminum tube was used, nine sealed samples were prepared. Under the respective temperature conditions, the unopened sealed samples were opened 4 weeks later, 8 weeks later and 13 weeks later, and samples for analysis were then collected.

TABLE 3

| Example No. | Temperature | 4 weeks later | 8 weeks later | 13 weeks later |
|---|---|---|---|---|
| Example 1 | 40° C. | 90.7 | 88.9 | 93.2 |
|  | room temp. | 93.4 | 90.3 | 92.0 |
|  | 4° C. | 95.1 | 93.0 | 94.9 |
| Example 2 | 40° C. | 89.0 | 87.0 | 86.2 |
|  | room temp. | 92.0 | 87.9 | 88.6 |
|  | 4° C. | 93.2 | 91.2 | 91.6 |
| Comparative Example 1 | 40° C. | 83.5 | 80.9 | 80.7 |
|  | room temp. | 86.6 | 88.0 | 82.1 |
|  | 4° C. | 89.5 | 86.8 | 88.7 |
| Comparative Example 2 | 40° C. | 85.0 | 85.3 | 81.4 |
|  | room temp. | 89.3 | 86.5 | 86.9 |

EXAMPLE 4

An oil-in-water type lotion having a formulation shown in Table 4 was prepared. The lotion was filled in the pouch-type aerosol container and the storage test for four weeks and eight weeks was performed as in Example 2 except that a nitrogen gas was used as a propellant.

TABLE 4

| Components | Content (% by weight) |
|---|---|
| Carboxyvinyl polymer | 0.25 |
| Propylene glycol | 5.0 |
| Methylparaben | 0.15 |
| Sodium hydroxide | 0.041 |
| Ascorbic acid | 0.1 |
| Glyceryl monostearate & PEG 100 Stearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |
| Higher alkyl benzoic acid ester | 4.0 |
| Benzyl alcohol | 0.3 |
| Ethyl alcohol | 5.0 |
| Disodium edetate | 0.05 |

TABLE 4-continued

| Components | Content (% by weight) |
|---|---|
| Retinol | 0.075 |
| Purified water | q.s. |
| Total | 100 |

COMPARATIVE EXAMPLE 3

The lotion prepared in Example 3 was filled in a jar container and the storage test for four weeks and eight weeks was performed as in Example 3. The results of Example 3 and Comparative Example 3 are shown in Table 5.

TABLE 5

| Example No. | Temperature | 4 weeks later | 8 weeks later |
|---|---|---|---|
| Example 3 | 40° C. | 95.7 | 94.9 |
|  | room temp. | 96.4 | 96.0 |
|  | 4° C. | 97.0 | 99.9 |
| Comparative Example 3 | 40° C. | 70.0 | 62.8 |
|  | room temp. | 94.6 | 90.3 |
|  | 4° C. | 96.1 | 98.9 |

EXAMPLE 4

An oil-in-water type lotion having the formulation shown in Table 6 was prepared.

TABLE 6

| Components | Content (% by weight) |
|---|---|
| Carboxyvinyl polymer | 0.3 |
| Propylene glycol | 5.0 |
| Methylparaben | 0.15 |
| Sodium hydroxide | 0.041 |
| Ascorbic acid | 0.1 |
| Glyceryl monostearate & PEG 100 Stearate | 5.0 |
| Cetanol | 1.0 |
| Stearyl alcohol | 0.5 |
| White Petrolatum | 1.5 |
| BHT | 0.05 |
| Propylparaben | 0.1 |
| Butylparaben | 0.05 |
| Cetyl palmitate | 1.0 |
| Higher alkyl benzoic acid ester | 4.0 |
| Benzyl alcohol | 0.3 |
| Ethyl alcohol | 5.0 |
| Disodium edetate | 0.05 |
| Retinol | 0.075 |
| Purified water | q.s. |
| Total | 100 |

The storage test was performed in the same manner as in Example 1 except that a two-compartment container whose propellant is LPG was used and that the distribution of the skin care composition is performed in an atmosphere of an inert gas. The results are shown in Table 7.

COMPARATIVE EXAMPLE 4

The lotion prepared in Example 4 was filled in a jar container and the storage test was performed as in Example 4. The results of Comparative Example 4 are shown in Table 7.

TABLE 7

| Example No. | Temperature | 4 weeks later | 8 weeks later | 13 weeks later |
|---|---|---|---|---|
| Example 4 | 40° C. | 92.6 | 89.2 | 87.4 |
|  | room temp. | 93.4 | 90.7 | 91.0 |
|  | 4° C. | 98.1 | 95.2 | 93.5 |
| Comparative Example 4 | 40° C. | 81.1 | 77.6 | 52.5 |
|  | room temp. | 91.0 | 82.6 | 84.8 |
|  | 4° C. | 92.4 | 91.7 | 92.7 |

EXAMPLE 5

A formulation was prepared in accordance with the procedure set forth in Example 1, except that the following components were used.

| | Content (% by weight) | |
|---|---|---|
| Components | Formula A | Formula B |
| Deionized Water | Q.S | Q.S |
| Sorbitol | 5.0 | 5.00 |
| Methylparaben | 0.15 | 0.15 |
| Disodium EDTA | 0.02 | 0.02 |
| Span 60 | 3.00 | 3.00 |
| Tween 60 | 4.00 | 4.00 |
| Beeswax | 0.95 | 0.95 |
| Safflower oil | 3.33 | 0.00 |
| Liquid Paraffin | 4.94 | 8.27 |
| BHT | 0.03 | 0.03 |
| Propylparaben | 0.10 | 0.10 |
| Fragrance | 0.15 | 0.15 |
| Retinol 40% | 0.37 | 0.37 |

The formulations A and B were divided into two. One portion each of formulation A and B was held at 40° C.; one portion each of formulation A and B was held at 50° C. for one week. After one week, stability of the retinol was measured. The results are set forth in Table 8 below. It can be seen that, after one week, formulation A, which contains safflower oil, an unsaturated oil, has significantly less retinol than that of formulation B, which does not contain unsaturated safflower oil.

TABLE 8

| | | % Retinol From Initial | |
|---|---|---|---|
| Weeks | Temperature | Formula A | Formula B |
| 1 | 40° C. | 89.0 | 92.0 |
|  | 50° C. | 84.0 | 91.5 |

EXAMPLE 6

The formulations of this example 6 were prepared by the procedure set forth in Example 1.

| Component | 6-I | 6-II | 6-III | 6-IV | 6-V |
|---|---|---|---|---|---|
| Vitamin A Alcohol | 0.166 | 0.166 | 0.166 | 0.166 | 0.166 |
| Carbomer | 0.30 | 0.30 | 0.30 | 0.30 | 0.30 |
| Propylene Glycol | 5.00 | 5.00 | 5.00 | 5.00 | 5.00 |
| Methyl Paraben | 0.15 | 0.15 | 0.15 | 0.15 | 0.15 |

-continued

| Component | 6-I | 6-II | 6-III | 6-IV | 6-V |
|---|---|---|---|---|---|
| Sodium Hydroxide 10% solution | 1.00 | 1.00 | 1.00 | 1.00 | 1.00 |
| Ascorbic Acid | — | — | — | — | 0.10 |
| Glyceryl Stearate & PEG-100 Stearate | 5.00 | 5.00 | 5.00 | 5.00 | 5.00 |
| Cetyl Alcohol | 1.00 | 1.00 | 1.00 | 1.00 | 1.00 |
| Stearyl Alcohol | 0.50 | 0.50 | 0.50 | 0.50 | 0.50 |
| White Petrolatum | 1.50 | 1.50 | 1.50 | 1.50 | 1.50 |
| Butylated Hydroxy-toluene | — | — | 0.05 | 0.05 | 0.05 |
| Propyl Paraben | 0.10 | 0.10 | 0.10 | 0.10 | 0.10 |
| Butyl Paraben | 0.05 | 0.05 | 0.05 | 0.05 | 0.05 |
| C12–15 Alkyl Benzoate | 4.00 | 4.00 | 4.00 | 4.00 | 4.00 |
| Cetyl Palmitate | 1.00 | 1.00 | 1.00 | 1.00 | 1.00 |
| Benzyl Alcohol | 0.30 | 0.30 | 0.30 | 0.30 | 0.30 |
| SD Alcohol 40-B | 5.00 | 5.00 | 5.00 | 5.00 | 5.00 |
| Disodium EDTA | — | 0.05 | — | 0.05 | 0.05 |
| Deionized Water | q.s. | q.s. | q.s. | q.s. | q.s. |

The stability of the formulations was measured by determining the amount of all-trans retinol after storage for various time periods at 40° C.

Figure 4:
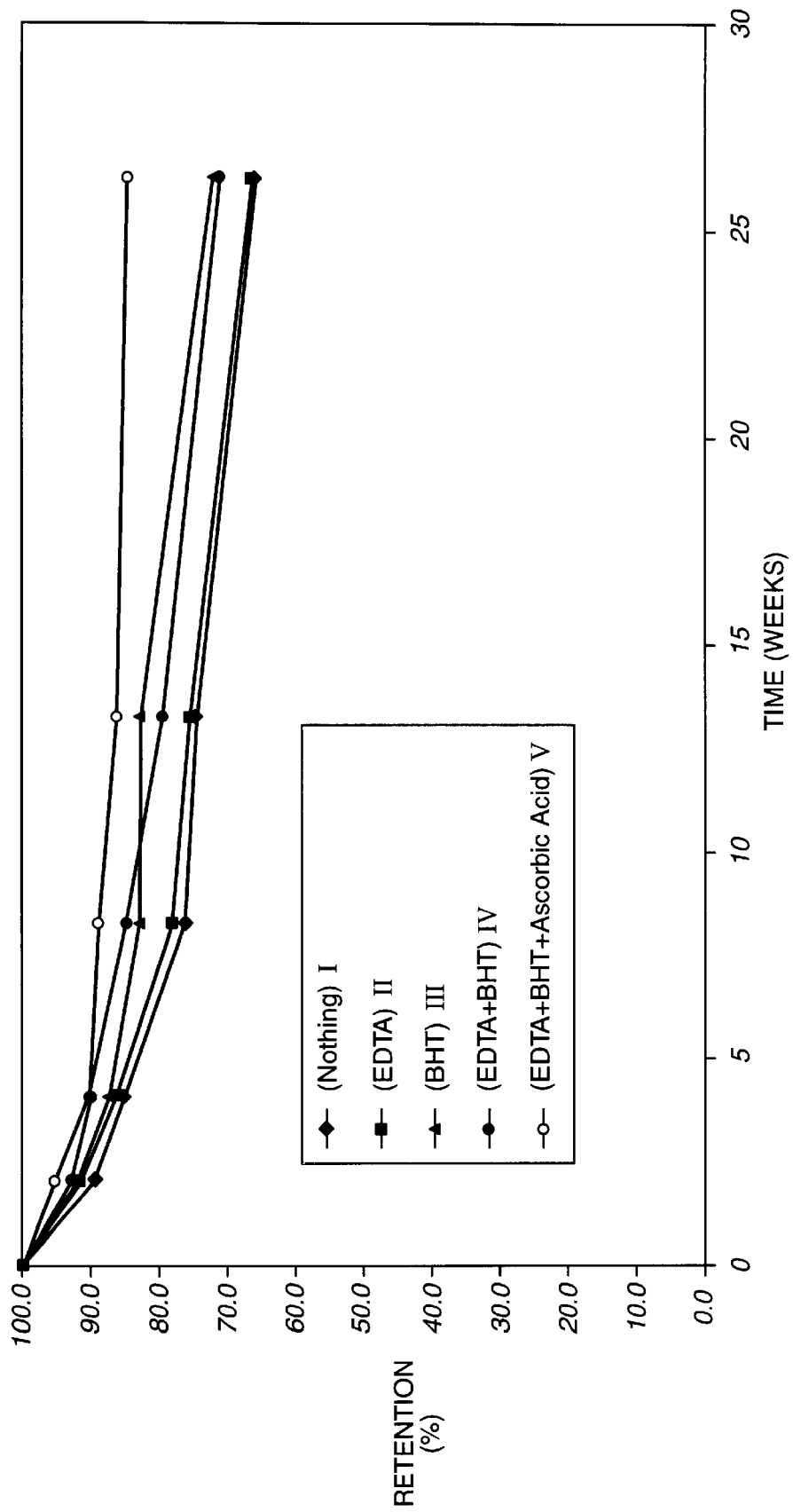
FIG. 4 is a graph representing retinol stability in different anti-oxidants at 40° C.

The results of this Example 6 are set forth in the graph in FIG. 4 hereto. After 13 weeks of aging, all the Formulations I–V retained at least 70% of the initial all-trans retinol in the compositions. The addition of a chelator, EDTA in Formulation 6-II improved the stability to a small extent. The addition of BHT, an oil-soluble anti-oxidant, in Formulation 6-III resulted in a relatively large improvement in stability. The use of both EDTA and BHT in Formulation 6-IV also resulted in another improvement. The use of a chelator, an oil-soluble anti-oxidant and ascorbic acid, a water-soluble anti-oxidant, in Formulation 6-V, resulted in an excellent stability, retaining approximately 90 of the initial all-trans retinol not only at 13 weeks, but at 25 weeks as well.

EXAMPLE 7

Another formulation in accordance with this invention contains the following ingredients:

| Ingredient | % W/W |
|---|---|
| Deionized Water | 83.38 |
| Carbomer | 0.35 |
| Methylparaben | 0.20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 1.00 |
| Dimethicone 100 cs | 1.00 |
| Cetyl Alcohol | 2.50 |
| Cetearyl Alcohol & Cetearyl Glucoside | 1.40 |
| BHT | 0.10 |
| Tocopherol Acetate | 0.50 |
| Propylparaben | 0.10 |
| Triethanolamine 99% | 0.40 |
| Tocopherol | 0.05 |
| Retinol 40% | 0.118 |
| Japanese Tea Extract | 1.00 |
| Diazolidinyl Urea | 0.30 |

The formulation of this Example 7 was found to be quite stable and is an acceptable emulsion for use on the face and other skin.

EXAMPLE 8

Another formulation in accordance with this invention contains the following ingredients:

EXAMPLE 8-I

| Ingredient | % W/W |
|---|---|
| Deionized Water | q.s. |
| Carbomer | 0.35 |
| Methylparaben | 0.20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 1.00 |
| Dimethicone 100 cs | 1.00 |
| Cetyl Alcohol | 2.50 |
| Cetearyl Alcohol & Cetearyl Glucoside | 1.40 |
| BHT | 0.10 |
| Tocopherol Acetate | 0.50 |
| Propylparaben | 0.10 |
| Deionized Water | 1.50 |
| Triethanolamine 99% | 0.40 |
| Tocopherol | 0.05 |
| Retinol 40% | 0.3825 |
| Japanese Tea Extract | 1.00 |
| Deionized Water | 2.00 |
| Diazolidinyl Urea | 0.30 |

The formulation of this Example 8-I is quite stable and is an acceptable emulsion for use on the face and other skin. After thirteen weeks of storage at 40 C, 97% of the initial level of all-trans retinol was present in the composition of this example.

Another formulation was prepared in accordance with the procedure of this example, having the following formulation:

EXAMPLE 8-II

| Ingredient | % W/W |
|---|---|
| Deionized Water | q.s. |
| Carbomer | 0.35 |
| Methylparaben | 0.20 |
| Disodium EDTA | 0.10 |
| D-Panthenol | 0.50 |
| Glycerin | 3.00 |
| C12–15 Alkyl Benzoate | 4.00 |
| Octyl Hydroxystearate | 2.00 |
| Cetyl Alcohol | 2.50 |
| Cetearyl Glucoside | 2.50 |
| BHT | 0.10 |
| Tocopherol Acetate | 0.50 |
| Propylparaben | 0.10 |
| Deionized Water | 1.50 |
| Triethanolamine 99% | 0.40 |
| Tocopherol | 0.05 |
| Retinol 40% | 0.3825 |
| Japanese Tea Extract | 1.00 |
| Deionized Water | 2.00 |
| Diazolidinyl Urea | 0.30 |

The formulation of this Example 8-II is quite stable and is an acceptable emulsion for use on the face and other skin. After thirteen weeks of storage at 40° C., 88% of the initial level of all-trans retinol was present in the composition of this example.

EXAMPLE 9A

A sunscreen-containing formulation may be made in accordance with the procedure set forth in Example 1, containing retinol and an active inorganic sunscreen ingredient, titanium dioxide. The formulation of this example is as follows:

| Ingredient | % W/W |
|---|---|
| Deionized Water | q.s. |
| Carbomer | 0.350 |
| Glycerine | 3.00 |
| Panthenol | 0.50 |
| Disodium EDTA | 0.10 |
| C12–15 Alkyl Benzoate | 4.00 |
| Octyl hydroxystearate | 12.00 |
| Titanium Dioxide | 4.00 |
| Dimethicone | 1.00 |
| Cetearyl alcohol and cetearyl glucoside | 1.40 |
| Retinol 10% | 0.46 |
| Cetyl Alcohol | 2.50 |
| Tocopheryl Acetate | 0.50 |
| Butylated Hydroxytoluene | 0.10 |
| Triethanolamine | 0.40 |
| Polysorbate 20 | 0.102 |
| Propyl paraben | 0.10 |
| Tocopherol | 0.05 |
| Paraben blend | 0.40 |

EXAMPLE 9B

Another formulation was created containing an organic sunscreen and retinol. The organic sunscreen used was octyl methoxycinnamate. This formulation had sunblock activity as well as having the other attributes of retinoid-containing formulations. The formulation was as follows:

| Ingredient | % W/W |
|---|---|
| Deionized Water | 66.84 |
| Glycerine | 5.00 |
| Panthenol | 0.50 |
| Disodium EDTA | 0.20 |
| Allantoin | 0.15 |
| Carbomer | 0.30 |
| Sodium metabisulfite | 0.10 |
| Octyl Methoxycinnamate | 6.00 |
| Glyceryl Stearate & PEG-100 Stearate | 5.00 |
| C12–C15 Alkyl Benzoate | 4.00 |
| White Petrolatum | 1.50 |
| Lauroyl Lysine | 1.00 |
| Cetyl Alcohol | 1.00 |
| Cetyl Palmitate | 1.00 |
| Stearyl Alcohol | 0.50 |
| Retinol 10% | 0.46 |
| Butylated Hydroxytoluene | 0.05 |
| SD Alcohol 40-B | 5.00 |
| Sodium Hydroxide | 1.00 |
| Isopropylparaben, Isobutylparaben, N-Butylparaben | 0.40 |

EXAMPLE 10

In yet another formulation, a retinol-containing composition was made for topical use. The composition was made in accordance with Example 1 above. The ingredients were as follows:

| Ingredient | % W/W |
|---|---|
| Deionized Water | 72.84 |
| Glycerine | 5.00 |
| Panthenol | 0.50 |
| Disodium EDTA | 0.20 |
| Allantoin | 0.15 |
| Carbomer | 0.30 |
| Sodium metabisulfite | 0.10 |
| Glyceryl Stearate & PEG-100 Stearate | 5.00 |
| C12–C15 Alkyl Benzoate | 4.00 |
| White Petrolatum | 1.50 |
| Lauroyl Lysine | 1.00 |
| Cetyl Alcohol | 1.00 |
| Cetyl Palmitate | 1.00 |
| Stearyl Alcohol | 0.50 |
| Retinol 10% | 0.46 |
| Butylated Hydroxytoluene | 0.05 |
| SD Alcohol 40-B | 5.00 |
| Sodium Hydroxide | 1.00 |
| Isopropylparaben, Isobutylparaben, N-Butylparaben | 0.40 |

EXAMPLE 11

Formulations in accordance with this invention may also be made containing azole-type compounds, such as itraconazole, miconazole and ketoconazole. The nitrate or other salt forms of the imidazoles should not be used, however, as they tend to render unstable the retinoids contained in the formulations. In this example, the following ingredients were combined to make imidazole-containing formulations according to the teachings of this invention.

| | % W/W | | |
|---|---|---|---|
| Ingredient | 11-I | 11-II | 11-III |
| Water Phase | | | |
| Deionized Water | q.s. 100 | q.s. 100 | q.s. 100% |
| Carbomer 940 | 0.22 | 0.22 | 0.22 |
| Disodium EDTA dihydrate | 0.10 | 0.10 | 0.10 |
| Propylene Glycol | 5.00 | 5.00 | 5.00 |
| Oil Phase | | | |
| Arlacel 165 | 5.0 | 5.0 | 5.0 |
| Cetyl Alcohol | 1.0 | 1.0 | 1.0 |
| Stearyl Alcohol | 0.5 | 0.5 | 0.5 |
| White Petrolatum | 1.5 | 1.5 | 1.5 |
| BHT | 0.05 | 0.05 | 0.05 |
| Methylparaben | 0.15 | 0.15 | 0.15 |
| Propylparaben | 0.1 | 0.1 | 0.1 |
| Butylparaben | 0.05 | 0.05 | 0.05 |
| C12–15 Alkyl benzoate | 4.0 | 4.0 | 4.0 |
| Cetyl Palmitate | 1.0 | 1.0 | 1.0 |
| Ketoconazole | 2.0 | — | — |
| Miconazole base | — | 2.0 | — |
| Miconazole nitrate | — | — | 2.0 |
| Ethyl Alcohol | 5.0 | 5.0 | 5.0 |
| Benzyl Alcohol | 0.3 | 0.3 | 0.3 |
| Retinol 40% | 0.332 | 0.332 | 0.332 |
| Sodium Hydroxide (adjust pH) | | | |

The formulations were made in accordance with the procedures set forth in Example 1, except that the imidazoles were added to the oil phase immediately before phasing the oil phase into the water phase. The stability of formulation 11-I at thirteen weeks of storage at 40° C. was such that 82% of the initial retinol was present. In formulation 11-II, after four weeks, 90% of the initial retinol remained compared with 71% of the initial retinol in formulation 11-III after four weeks. Thus, good stability was achieved in imidazole-containing formulations according to this invention.

EXAMPLE 12

In another formulation, the following composition was prepared as an oil-in-water emulsion:

| Ingredient | % W/W |
|---|---|
| Water Phase | |
| Deionized Water | 65.74 |
| Carbopol 934 (carboxy-vinyl polymer) | 0.30 |
| Sodium EDTA | 0.05 |
| Sodium bisulfite | 0.10 |
| Butyl Paraben | 0.05 |
| Methyl Paraben | 0.15 |
| Propyl Paraben | 0.01 |
| Allantoin | 0.15 |
| Panthenol | 0.50 |
| Propylene Glycol | 5.00 |
| Oil Phase | |
| Arlacel 165 | 5.00 |
| Cetyl Alcohol | 1.00 |
| Stearyl Alcohol | 1.50 |
| White Petrolatum | 1.50 |
| Octyl Methoxycinnamate | 6.00 |
| BHT | 0.05 |
| C12–15 Alkyl Benzoates | 4.00 |
| Cetyl Palmitate | 1.00 |
| Retinol Phase | |
| Sodium Hydroxide @ 10% (solution w/w) | 1.00 |
| Ethyl Alcohol | 5.00 |
| Benzyl Alcohol | 0.30 |
| Lauroyl lysine | 1.00 |
| Retinol 10% | 1.59 |

Deionized water was weighed into a suitable beaker. Nitrogen gas was bubbled through water, heat was applied and the water was mixed. At high speed mixing, Carbomer was slowly added to deionized water, and mixed for five minutes. The Disodium EDTA and sodium bisulfite were added to this mixture. At 60° C., methyl, propyl, and butyl paraben were added, in addition to allantoin and panthenol and the mixing continued. At 80° C., propylene glycol was added and the composition mixed.

In a separate beaker, the oil phase ingredients were weighed one by one while heat was applied. The mixture was heated to 80° C. and mixed until homogeneous. The oil mixture was phased into the water phase slowly with mixing, and cooling was begun. At 60° C., the sodium hydroxide, lauroyl lysine and Retinol were added individually. At about 35° C., ethyl alcohol and benzyl alcohol were added and mixing continued for about 10 minutes. Water was added q.s. and the formulation mixed for about five minutes until the batch was homogeneous.

The pH of the formulation of this example was about 6.6. The batch appeared creamy, glossy, smooth, homogeneous and off-white.

EXAMPLE 13

Retinaldehyde-containing compositions were made in accordance with the following procedure. Operating under yellow light and an argon gas blanket, deionized water was weighed out in a beaker. Carbomer was slowly added and the composition mixed well until dispersed. Disodium EDTA and methyl paraben were added to the mixture and the mixture was heated to 80° C. At 80° C., propylene glycol was added. The oil phase ingredients were weighed and placed into a separate beaker. The mixture was heated to 80° C. with stirring and dimethicone added. With both phases at 80° C., the oil phase was added to the water phase and mixed. In formulation 13-I, a 50% sodium hydroxide solution was added for pH adjustment. Prior to adding the retinaldehyde, the mixture was held at 80° C. for ten minutes, then cooled to 30° C. Retinaldehyde was mixed with benzyl alcohol and added to the mixture. In formulation 13-II, citral was added to the premixture containing benzyl alcohol and retinaldehyde.

| | % W/W | |
|---|---|---|
| Ingredient | 13-I | 13-II |
| Water Phase | | |
| Deionized Water | 82.29 | 82.29 |
| Carbomer 941 (carboxy-vinyl polymer) | 0.30 | 0.30 |
| Propylene Glycol | 4.00 | 4.00 |
| Methylparaben | 0.30 | 0.30 |
| Disodium EDTA | 0.10 | 0.10 |
| Oil Phase | | |
| Myristyl Myristate | 1.50 | 1.50 |
| Glyceryl Stearate | 1.25 | 1.25 |
| stearic Acid | 1.25 | 1.25 |
| Oleic Acid | 1.25 | 1.25 |
| Polysorbate 61 | 1.20 | 1.20 |
| Isopropyl Palmitate | 1.00 | 1.00 |
| Stearoxytrimethylsilane | 1.00 | 1.00 |
| Dimethicone | 1.00 | 1.00 |
| Sorbitan Stearate | 0.80 | 0.80 |
| Synthetic Beeswax | 0.50 | 0.50 |
| Cetyl Alcohol | 0.50 | 0.50 |
| Stearyl Alcohol | 0.50 | 0.50 |
| BHT | 0.02 | 0.02 |
| Propylparaben | 0.10 | 0.10 |
| Butylparaben | 0.05 | 0.05 |
| Benzyl Alcohol | 0.30 | 0.30 |
| Sodium Hydroxide | 0.2 | 0.2 |
| Citral | — | 1.6 |
| Retinaldehyde | 0.05 | 0.05 |

Two other formulations containing retinaldehyde were made as follows. Deionized water was weighed into a beaker and with mixing at high speed, carbomer was added slowly. After a few minutes, EDTA was added, as well as ascorbic acid. Mixing was continued for about 45 minutes until the mixture was uniform. The mixture was heated to 80° C. and propylene glycol added. In a separate beaker all oil phase ingredients were placed. The beaker was heated to 80° C. with mixing until homogeneous. The oils were then slowly phased into the water phase with mixing. Sodium hydroxide was added at 80° C. and the emulsion mixed for about ten minutes. Cooling was begun. At 35° C., benzyl alcohol was added. The batch was q.s. to 997 gm weight with water. The emulsion was mixed until uniform, about five minutes. The batch was then split into two portions. To one batch was added ethanol and retinaldehyde which had been premixed and dissolved. To the second batch was added a premix of ethanol, citral and retinaldehyde. The batches were then filled into blind aluminum tubes and stored at 40° C. for thirteen weeks. The formulations were as follows:

| | % W/W | |
|---|---|---|
| Ingredient | 13-III | 13-IV |
| Water Phase | | |
| Deionized Water | 75.85 | 74.25 |
| Carbomer 934P | 0.30 | 0.30 |
| Disodium EDTA | 0.05 | 0.05 |

-continued

| Ingredient | % W/W | |
|---|---|---|
| | 13-III | 13-IV |
| Ascorbic Acid | 0.10 | 0.10 |
| Propylene Glycol | 5.00 | 5.00 |
| Oil Phase | | |
| Glyceryl Monostearate & PEG 100 Stearate | 5.0 | 5.0 |
| Cetyl Alcohol | 1.0 | 1.0 |
| Stearyl Alcohol | 0.5 | 0.5 |
| White Petrolatum | 1.5 | 1.5 |
| BHT | 0.05 | 0.05 |
| Methylparaben | 0.15 | 0.15 |
| Propylparaben | 0.1 | 0.1 |
| Butylparaben | 0.05 | 0.05 |
| C12–15 Alkyl benzoate | 4.0 | 4.0 |
| Cetyl Palmitate | 1.0 | 1.0 |
| Sodium Hydroxide 10% (w/w soln.) | 1.0 | 1.0 |
| Ethyl Alcohol | 4.0 | 4.0 |
| Benzyl Alcohol | 0.3 | 0.3 |
| Retinaldehyde | 0.05 | 0.05 |
| Citral | — | 1.6 |

All four formulations of this example were stored for thirteen weeks at 40° C. and had the following stabilities:

| Stability | 13-I | 13-II | 13-III | 13-IV |
|---|---|---|---|---|
| Conditions 13 wk/40° C. | 65% | 53% | 65% | 69% |

It is believed that, although the instability of retinal is even greater than that of retinol, through use of the methods and formulations of this invention, the stability can be improved. For example, an increase in pH in these formulations will result in an improved stability. In examples 13-I and 13-II, the C-value should be reduced as well.

EXAMPLE 14

Skin care compositions containing retinol with and without octylmethoxycinnamate were prepared in an oil-in-water emulsion having the formulations set forth below. The method of preparation was similar to those of preceding examples.

| | 14A | 14B |
|---|---|---|
| Distilled Water | 64.45 | 70.45 |
| Carbomer | 0.3 | 0.3 |
| Glycerin | 5.0 | 5.0 |
| Panthenol, DL | 0.5 | 0.5 |
| Allantoin | 0.15 | 0.15 |
| Sodium metabisulfite | 0.1 | 0.1 |
| Disodium EDTA | 0.2 | 0.2 |
| Octylmethoxycinnamate | 6.0 | 0.0 |
| Glyceryl Stearate & PEG 100 Stearate | 5.0 | 5.0 |
| C12–C15 Alkyl Benzoate | 4.0 | 4.0 |
| White Petrolatum | 1.5 | 1.5 |
| Lauroyl Lysine | 1.0 | 1.0 |
| Cetyl Alcohol | 1.0 | 1.0 |
| Cetyl Palmitate | 1.0 | 1.0 |
| Stearyl Alcohol | 0.5 | 0.5 |
| Butylated Hydroxytoluene | 0.05 | 0.05 |
| SD Alcohol 40B | 5.0 | 5.0 |
| Retinol | 0.165 | 0.165 |
| Soybean Oil | 1.485 | 1.485 |
| Sodium hydroxide solution | 1.0 | 1.0 |
| Paraben mixture and phenoxyethanol | 1.5 | 1.5 |
| Methyldihydrojasmonate | 0.1 | 0.1 |

Examples 14A and 14B were submitted for human clinical studies to evaluate the irritation potential of the formulations. Products were repeatedly placed on subjects' backs (n=200) under occlusion for a period of three successive weeks. Between applications of fresh product, the intensity of the irritation caused by the products was scored on a 0–4 grading scale (0 representing no irritation and 4 representing intense erythema with edema and vesiculation). The irritation score for the retinol containing product without octylmethoxycinnamate (14B) was 267. For the product containing octylmethoxycinnamate (14A), the irritation score was 95, approximately one-third that of the product without the octylmethoxycinnamate. A second pair of formulae, with and without octylmethoxycinnamate were compounded to repeat this test and to confirm this observation, as follows:

| | 14C | 14D |
|---|---|---|
| Distilled Water | 68.075 | 74.075 |
| Carbomer | 0.3 | 0.3 |
| Glycerin | 5.0 | 5.0 |
| Panthenol, DL | 0.5 | 0.5 |
| Allantoin | 0.15 | 0.15 |
| Disodium EDTA | 0.2 | 0.2 |
| Water & Thea Sinensis (green tea) Extract | 1.0 | 1.0 |
| Octylmethoxycinnamate | 6.0 | 0.0 |
| Glyceryl Stearate & PEG 100 Stearate | 5.0 | 5.0 |
| C12–C15 Alkyl Benzoate | 4.0 | 4.0 |
| White Petrolatum | 1.5 | 1.5 |
| Lauroyl Lysine | 0.5 | 0.5 |
| Cetyl Alcohol | 1.0 | 1.0 |
| Cetyl Palmitate | 1.0 | 1.0 |
| Stearyl Alcohol | 0.5 | 0.5 |
| Butylated Hydroxytoluene | 0.05 | 0.05 |
| SD Alcohol 40B | 2.5 | 2.5 |
| Retinol | 0.165 | 0.165 |
| Soybean Oil | 1.485 | 1.485 |
| Sodium hydroxide solution (20%) | 0.675 | 0.675 |
| Isopropyl, isobutyl, & butylparabens | 0.4 | 0.4 |

A similar test was conducted with n=52 subjects. The irritation score for the product without the octylmethoxycinnamate (14D) was 105.5, and for the product with the octylmethoxycinnamate (14C) the irritation score was only 40.5, again, approximately one-third that of the formula without the octylmethoxycinnamate.

These results are particularly unexpected as octylmethoxycinnamate is considered to be a potentially irritating material. Previous irritation tests demonstrate that addition of octylmethoxycinnamate at 6% to a formula which did not contain a retinoid increases the level of irritation. Two products were prepared as follows:

|  | 14E | 14F |
| --- | --- | --- |
| Distilled Water | 65.66 | 71.88 |
| Carbomer | 0.3 | 0.3 |
| Glycerin | 5.0 | 5.0 |
| Panthenol, DL | 0.5 | 0.5 |
| Allantoin | 0.15 | 0.15 |
| Sodium metabisulfite | 0.1 | 0.1 |
| Disodium EDTA | 0.2 | 0.2 |
| Octylmethoxycinnamate | 6.0 | 0.0 |
| Glyceryl Stearate & PEG 100 Stearate | 5.0 | 5.0 |
| C12–C15 Alkyl Benzoate | 4.0 | 4.0 |
| White Petrolatum | 1.5 | 1.5 |
| Lauroyl Lysine | 1.0 | 1.0 |
| Cetyl Alcohol | 1.0 | 1.0 |
| Cetyl Palmitate | 1.0 | 1.0 |
| Stearyl Alcohol | 0.5 | 0.5 |
| Butylated Hydroxytoluene | 0.05 | 0.05 |
| SD Alcohol 40B | 5.0 | 5.0 |
| Soybean Oil | 0.44 | 0.22 |
| Sodium hydroxide solution | 1.0 | 1.0 |
| Paraben mixture and phenoxyethanol | 1.5 | 1.5 |
| Methyldihydrojasmonate | 0.1 | 0.1 |

These formulae were also tested as indicated above in patch tests on human subject backs (n=200). The irritation scores for the product without the octylmethoxycinnamate (14F) was 21.5, while the irritation score for the product with 6% octylmethoxycinnamate (14E) was 52, more than twice as irritating. Unexpectedly, however, it appears that in formulae containing retinol, the addition of octylmethoxycinnamate mitigates the irritation of the product.

EXAMPLE 16

A formulation in accordance with this invention was made using the following ingredients, which compose a base vehicle for use in the compositions of this invention:

| Component CTFA Name | % (w/w) |
| --- | --- |
| Deionized Water | 78.285 |
| Glycerin | 5.000 |
| Carbomer | 0.300 |
| Disodium EDTA | 0.200 |
| Sodium Hydroxide | 0.135 |
| Alcohol | 2.780 |
| Methylparaben | 0.230 |
| Propylparaben | 0.070 |
| Glyceryl Stearate & PEG 100 Stearate | 5.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Total | 100.00 |

The water phase was prepared by measuring formula weight of water into a suitable vessel. The carbomer was slowly introduced to allow for hydration. The vessel was then heated to about 70° C. At 70° C., glycerin and EDTA were added. The composition was held at this temperature and mixed until the ingredients were dissolved. The water phase was then neutralized with TEA. The oil phase was then prepared separately by measuring all oil soluble ingredients into a suitable vessel, as follows: C12–15 alkyl benzoate, glyceryl stearate and PEG 100 stearate, white petrolatum, cetyl palmitate, cetyl alcohol and stearyl alcohol. The oil phase was then heated to 70° C. and the propylparaben and methyl paraben were added. The water phase was then slowly introduced to the oil phase, forming the emulsion. The emulsion was permitted to cool. When the temperature of the emulsion reached 35° C., the alcohol was added and the emulsion mixed until uniform. The batch was weighed and water added to compensate for evaporation upon heating. pH was measured and adjusted.

Alternatively, the process for making the foregoing formulation may be carried out by adding the oil phase to the water phase. However, generally, better physical stability is achieved when the water phase is added to the oil phase.

EXAMPLE 17

A formulation in accordance with this invention was made using the following ingredients:

| Component CTFA Name | % (w/w) |
| --- | --- |
| Deionized Water | 85.95 |
| Carbomer | 0.350 |
| Methylparaben | 0.200 |
| Disodium EDTA | 0.100 |
| Glycerin | 3.000 |
| C12–15 Alkyl Benzoate | 4.000 |
| Octyl Hydroxystearate | 1.000 |
| Dimethicone | 1.000 |
| Cetyl Alcohol | 2.500 |
| Cetearyl Alcohol and Cetearyl Glucoside | 1.400 |
| Propylparaben | 0.100 |
| Triethanolamine | 0.400 |
| Total | 100.00 |

The water phase was prepared by measuring formula weight of water into suitable vessel. Carbomer was introduced slowly to allow for hydration. The phase was heated to 75° C. At temperature, glycerin and EDTA were added. The temperature was held and the phase mixed until the ingredients were dissolved. The oil phase was prepared by measuring formula weight of the oil soluble ingredients into a suitable vessel, as follows: C12–15 Alkyl Benzoate, Octyl hydroxystearate, Dimethicone, Cetyl Alcohol, Cetearyl Alcohol and Cetearyl Glucoside.

The oil phase was heated to 75° C. and the propylparaben and the methylparaben added. With the temperature of both phases at 75° C., the oil phase was slowly introduced to the water phase. The system was neutralized with TEA. The batch was homogenized for a minimum of 1 minute. The steps of introducing the phases coupled with homogenization, resulted in emulsion formation. The batch was weighed and water added to compensate for evaporation upon heating. pH was measured and adjusted.

Alternatively, the process for making the foregoing formulation may be carried out by adding the oil phase to the water phase.

EXAMPLE 18

An emulsion was prepared in accordance with this invention which did not contain a lower alkyl alcohol or detackifying material. The emulsion was prepared in accordance with the procedure set forth in Example 15 and contained the following ingredients:

| Component CTFA Name | % (w/w) |
|---|---|
| Deionized Water | 73.055 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Phenoxyethanol | 0.700 |
| Methylparaben | 0.230 |
| Propylparaben | 0.070 |
| Glyceryl Stearate & PEG 100 Stearate | 5.000 |
| Octylmethoxy-cinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |

This formulation was functional as an emulsion, but exhibited some drag on application and tacky on drydown during application to the skin and was somewhat grainy in texture.

EXAMPLE 19

An emulsion in accordance with the compositions of this invention was prepared containing a detackifying material, lauroyl lysine, but without a lower alkyl alcohol, having the following ingredients:

| Component CTFA Name | % (w/w) |
|---|---|
| Deionized Water | 72.555 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Phenoxyethanol | 0.700 |
| Methylparaben | 0.230 |
| Propylparaben | 0.070 |
| Glyceryl Stearate & PEG 100 Stearate | 5.000 |
| Octylmethoxy-cinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

This formulation held together well and was visually esthetically pleasing, without graininess. Upon application to the skin, it was somewhat slow in spreading, but was non-tacky during drying.

EXAMPLE 20

An emulsion in accordance with the compositions of this invention was prepared containing a lower alkyl alcohol, but without a detackifying material, lauroyl lysine, having the following ingredients:

| Component CTFA Name | % (w/w) |
|---|---|
| Deionized Water | 70.275 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |
| Octylmethoxy-cinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |

This formulation was smooth in application but tacky and draggy while drying upon the skin, but had satisfactory appearance and esthetics.

EXAMPLE 21

An emulsion in accordance with the compositions of this invention was prepared containing both a lower alkyl alcohol, and a detackifying material, lauroyl lysine, having the following ingredients:

Component CTFA Name % (w/w)

| Component CTFA Name | % (w/w) |
|---|---|
| Deionized Water | 69.775 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |
| Octylmethoxy-cinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

This formulation had an excellent appearance, i.e., smooth and white, and was easy to spread and was not tacky upon drying on the skin.

EXAMPLE 22

A formulation was prepared having about 15 weight percent of ethyl alcohol, as follows:

| Component CTFA Name | % (w/w) |
|---|---|
| Deionized Water | 57.555 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Alcohol | 15.00 |
| Phenoxyethanol | 0.700 |
| Methylparaben | 0.230 |
| Propylparaben | 0.070 |
| Glyceryl Stearate & PEG 100 Stearate | 5.000 |
| Octylmethoxycinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

This formulation had an alcoholic odor and was somewhat wet in spreading upon application to the skin. It demonstrated that the level of alcohol should be about 15 weight percent or below in order to achieve an esthetic formulation.

EXAMPLE 23

A formulation was prepared having about 7 weight percent of lauroyl lysine, as follows:

| Component CTFA Name | % (w/w) |
|---|---|
| Deionized Water | 63.275 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |
| Octylmethoxycinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 7.000 |

This product was esthetically satisfactory, however, additional amounts of lauroyl lysine would most probably not provide additional esthetic benefit and may produce pastiness in the emulsion.

EXAMPLE 24

Several formulations were prepared to demonstrate the necessity of balancing the dry, emollient oil portion of the oil phase with the substantive oil or wax portion of the oil phase in order to achieve an esthetic formulation. Composition 24A contained neither dry, emollient oil nor substantive oil or wax. Composition 24B contained only a substantive oil or wax, octyl hydroxystearate. Composition 24C contained a dry emollient oil, C12–15 alkyl benzoate. Composition 24D contained both hydroxystearate and C12–15 alkyl benzoate. The compositions were as follows:

| | 24A | 24B | 24C | 24D |
|---|---|---|---|---|
| Deionized Water | 89.498 | 88.498 | 85.498 | 84.498 |
| Carbomer | 0.350 | 0.350 | 0.350 | 0.350 |
| Disodium EDTA | 0.100 | 0.100 | 0.100 | 0.100 |
| Panthenol | 0.500 | 0.500 | 0.500 | 0.500 |
| Glycerin | 3.000 | 3.000 | 3.000 | 3.000 |
| C12–15 Alkyl Benzoate | — | — | 4.000 | 4.000 |
| Octyl hydroxystearate | — | 1.000 | — | 1.000 |
| Dimethicone | 1.000 | 1.000 | 1.000 | 1.000 |
| Cetyl Alcohol | 2.500 | 2.500 | 2.500 | 2.500 |
| Cetearyl alcohol and Cetearyl glucoside | 1.400 | 1.400 | 1.400 | 1.400 |
| BHT | 0.100 | 0.100 | 0.100 | 0.100 |
| Vitamin E Acetate | 0.500 | 0.500 | 0.500 | 0.500 |
| Propylparaben | 0.100 | 0.100 | 0.100 | 0.100 |
| Triethanolamine | 0.400 | 0.400 | 0.400 | 0.400 |
| Tocopherol | 0.050 | 0.050 | 0.050 | 0.050 |
| Polysorbate | 0.102 | 0.102 | 0.102 | 0.102 |
| Paraben Blend | 0.400 | 0.400 | 0.400 | 0.400 |

It was found that compositions 24A was quite grainy in appearance and dry when applied to the skin. It did not provide for sufficient time to spread over the skin upon application as it dried immediately and would not be an acceptable skin care product. Composition 24B, which had no dry emollient oil was not easy to spread, leaving a heavy coated feeling on the skin. Composition 24C, which contained a dry emollient oil but no substantive oil or wax had a poor afterfeel as it dried too fast, lacking a feeling of substantive benefit, although it was easily spread over the skin. Composition 24D had both types of oil and exhibited a good balance of spreadability, absorbability and afterfeel.

EXAMPLE 25

Compositions were made which incorporated a high percentage of dry emollient oil and a high percentage of substantive oil, respectively, as follows:

| Ingredient | 25A | 25B |
|---|---|---|
| Deionized Water | 76.498 | 73.498 |
| Carbomer | 0.350 | 0.350 |
| Disodium EDTA | 0.100 | 0.100 |
| Panthenol | 0.500 | 0.500 |
| Glycerin | 3.000 | 3.000 |
| C12–15 Alkyl Benzoate | 12.000 | 4.000 |
| Octyl Hydroxystearate | 1.000 | 12.000 |
| Dimethicone | 1.000 | 1.000 |
| Cetyl Alcohol | 2.500 | 2.500 |
| Cetearyl Alcohol and Cetearyl Glucoside | 1.400 | 1.400 |
| BHT | 0.100 | 0.100 |
| Vitamin E Acetate | 0.500 | 0.500 |
| Propylparaben | 0.100 | 0.100 |
| Triethanolamine | 0.400 | 0.400 |
| Tocopherol | 0.050 | 0.050 |

-continued

| Ingredient | 25A | 25B |
|---|---|---|
| Polysorbate | 0.102 | 0.102 |
| Paraben Blend | 0.400 | 0.102 |

It was found that composition 25A, containing 12% C12–15 alkyl benzoate, had a greasy feeling, while composition 25B, containing 12% octyl hydroxystearate, had a "draggy" afterfeel and left a heavy residue.

EXAMPLE 26

A composition according to this invention may be made containing one or more vitamins, an antioxidant material, a sunscreen and a soothing/protectant compound as follows:

| Component CTFA Name | % (w/w) |
|---|---|
| Deionized Water | 69.775 |
| Glycerin | 5.000 |
| Panthenol | 0.500 |
| Allantoin | 0.150 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |
| Octylmethoxycinnamate | 6.000 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

EXAMPLE 27

A composition according to this invention may be made containing antiinflammatory compounds, including a steroidal compound, a non-steroidal compound and/or a naturally derived antiinflammatory compound, as follows:

Composition 27A:
Component CTFA Name % (w/w)

| Component CTFA Name | % (w/w) |
|---|---|
| Composition 27A: | |
| Deionized Water | 72.498 |
| Carbomer | 0.350 |
| Disodium EDTA | 0.100 |
| Panthenol | 0.500 |
| Glycerin | 3.000 |
| C12–15 Alkyl Benzoate | 4.000 |
| Octyl Hydroxystearate | 12.000 |
| Hydrocortisone and its respective salts | 1.000 |
| Dimethicone | 1.000 |
| Cetyl Alcohol | 2.500 |
| Cetearyl Alcohol and Cetearyl Glucoside | 1.400 |
| BHT | 0.100 |
| Vitamin E Acetate | 0.500 |
| Propylparaben | 0.100 |
| Triethanolamine | 0.400 |
| Tocopherol | 0.050 |
| Polysorbate 20 | 0.102 |
| Paraben Blend | 0.400 |
| Composition 27B: | |
| Deionized Water | 71.498 |
| Carbomer | 0.350 |
| Disodium EDTA | 0.100 |
| Panthenol | 0.500 |
| Glycerin | 3.000 |
| C12–15 Alkyl Benzoate | 4.000 |
| Octyl Hydroxystearate | 12.000 |
| Ibuprofen | 2.000 |
| Dimethicone | 1.000 |
| Cetyl Alcohol | 2.500 |
| Cetearyl Alcohol and Cetearyl Glucoside | 1.400 |
| BHT | 0.100 |
| Vitamin E Acetate | 0.500 |
| Propylparaben | 0.100 |
| Triethanolamine | 0.400 |
| Tocopherol | 0.050 |
| Polysorbate 20 | 0.102 |
| Paraben Blend | 0.400 |
| Composition 27C: | |
| Deionized Water | 70.298 |
| Japanese Green Tea Extract | 1.000 |
| Carbomer | 0.350 |
| Disodium EDTA | 0.100 |
| Panthenol | 0.500 |
| Glycerin | 3.000 |
| C12–15 Alkyl Benzoate | 4.000 |
| Octyl Hydroxystearate | 12.000 |
| Glycyrrhizic acid | 1.000 |
| Stearyl Glycyrrhetinate | 1.000 |
| Bisabolol | 0.200 |
| Dimethicone | 1.000 |
| Cetyl Alcohol | 2.500 |
| Cetearyl Alcohol and Cetearyl Glucoside | 1.400 |
| BHT | 0.100 |
| Vitamin E Acetate | 0.500 |
| Propylparaben | 0.100 |
| Triethanolamine | 0.400 |
| Tocopherol | 0.050 |
| Polysorbate 20 | 0.102 |
| Paraben Blend | 0.400 |

EXAMPLE 27

A composition according to this invention may be made which contains oil-soluble vitamins in combination with vitamin A palmitate, as follows:

| Component CTFA Name | % (w/w) |
|---|---|
| Deionized Water | 83.498 |
| Carbomer | 0.350 |
| Disodium EDTA | 0.100 |
| Panthenol | 0.500 |
| Glycerin | 3.000 |
| C12–15 Alkyl Benzoate | 4.000 |
| Octyl Hydroxystearate | 1.000 |
| Dimethicone | 1.000 |
| Cetyl Alcohol | 2.500 |

-continued

| Component CTFA Name | % (w/w) |
|---|---|
| Cetearyl Alcohol and Cetearyl Glucoside | 1.400 |
| BHT | 0.100 |
| Vitamin E Acetate | 0.500 |
| Propylparaben | 0.100 |
| Triethanolamine | 0.400 |
| Tocopherol | 0.050 |
| Vitamin A Alcohol | 0.102 |
| Vitamin A Palmitate | 1.000 |
| Paraben Blend | 0.400 |

EXAMPLE 28

A composition in accordance with this invention may be made which contains proteins and/or amino acids, as follows:

| Component CTFA Name | % (w/w) |
|---|---|
| Deionized Water | 69.075 |
| Glycerin | 5.000 |
| Panthenol | 0.500 |
| Allantoin | 0.150 |
| Sodium Hyaluronate | 0.200 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |
| Octylmethoxycinnamate | 6.000 |
| Hydrolyzed Collagen | 0.500 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

EXAMPLE 29

A composition in accordance with this invention may be made which incorporates natural extracts, such as saponins, flavonoids, tannins and the like, as follows:

| Component CTFA Name | % (w/w) |
|---|---|
| Deionized Water | 67.775 |
| Glycerin | 5.000 |
| Witch Hazel Extract | 1.000 |
| Panthenol | 0.500 |
| Allantoin | 0.150 |
| Fagus Silvatica Extract | 0.500 |
| Carbomer | 0.300 |
| Disodium EDTA | 0.200 |
| Sodium Hydroxide | 0.135 |
| Alcohol | 2.780 |
| Phenoxyethanol | 0.700 |
| Methylparaben | 0.230 |
| Propylparaben | 0.070 |
| Glyceryl Stearate & PEG 100 Stearate | 5.000 |

-continued

| Component CTFA Name | % (w/w) |
|---|---|
| Octylmethoxycinnamate | 6.000 |
| Pilewort Extract | 0.500 |
| C 12–15 Alkyl Benzoate | 4.000 |
| White Petrolatum | 1.500 |
| Cetyl Palmitate | 1.000 |
| Cetyl Alcohol | 1.000 |
| Stearyl Alcohol | 0.500 |
| Soybean Oil | 0.460 |
| BHT | 0.100 |
| Vitamin E Acetate | 0.100 |
| Lauroyl Lysine | 0.500 |

EXAMPLE 30

A composition was made which contains a retinol compound and depigmentation materials which is effective in producing even skin color, as follows:

| Ingredient | w/w % |
|---|---|
| Deionized water | 74.6102 |
| Hydroxyethylcellulose | 1.00 |
| Xanthan Gum | 0.20 |
| Disodium EDTA | 0.10 |
| D Panthenol | 0.50 |
| Glcyerin | 3.00 |
| Glutathione | 0.20 |
| Magnesium-L-ascorbyl-phosphate | 3.00 |
| Citric acid | 0.05 |
| C12–15 Alkyl benzoate | 4.00 |
| Octyl hydroxystearate | 1.00 |
| Dimethicone | 1.00 |
| Cetyl alcohol | 2.50 |
| Cetearyl glucoside | 1.40 |
| di-alpha tocopheryl acetate | 0.50 |
| Octyl methoxycinnamate | 4.00 |
| Methyl paraben | 0.2% |
| Propyl paraben | 0.0987% |
| Phenoxyethanol | 0.7333% |
| 10% Sodium hyroxide | 0.80 |
| di-alpha tocopherol | 0.05 |
| Vitamin A/Tween 45% Lecithin 70% Ascorbyl palmitate 25% | 0.0686 |
| Alpha tocopherol 5% | 0.001 |
| Tea leaf distilled solution | 1.00 |

EXAMPLE 31

Various irritation mitigation agents were evaluated in comparison with a control formulation, designated below as Example 31-Control. The formulations containing irritation mitigation agents were evaluated clinically using the procedure set forth in Example 14 to determine the extent to which irritation was mitigated with respect to the control formulation. The control formulation was as follows:

| Ingredient | Weight Percent |
|---|---|
| Retinol (10% in soybean oil) | 1.725 |
| Glyceryl Stearate & PEG 100 Stearate | 5.000 |
| C12–C15 Alkyl Benzoate | 4.000 |
| Petrolatum | 1.500 |
| Lauryl lysine | 0.500 |
| Cetyl alcohol | 1.000 |
| Cetyl Palmitate | 1.000 |

-continued

| Ingredient | Weight Percent |
|---|---|
| Stearyl Alcohol | 0.500 |
| BHT | 0.100 |
| Phenoxyethanol, methyl paraben and propylparaben | 1.000 |
| Vitamin E Acetate | 0.100 |
| Glcyerin | 5.000 |
| D Panthenol | 0.500 |
| Allantoin | 0.150 |
| Carbomer | 0.300 |
| Disodium EDTA | 0.200 |
| Sodium Hydroxide | 0.135 |
| Denatured Alcohol | 2.780 |
| Water | q.s. to 100 |

The irritation score for Example 31(31A)—Control formulation was 146 in the RIPT evaluation. Example 31B contained 5% by weight menthyl anthranilate and had an irritation score of 65 in a side-by-side test against Example 31A. Example 31C contained 5% by weight of homomenthyl salicylate. Example 31C resulted in an irritation score of 61.5. Example 31D contained 5% by weight of octocrylene. Example 31D resulted in an irritation score of 73.5. Example 31E contained 5% by weight of octyl dimethyl PABA. This formulation resulted in an irritation score of 68.5.

In order to compare oil-soluble irritation mitigation agents with water-soluble compounds, Examples 31F and 31G were formulated. Example 31F contained 5% by weight TEA-salicylate, a water-soluble organic ester. This formulation resulted in an irritation score of 177. Example 31G contained 5% by weight of DEA-methoxy cinnamate, another water-soluble organic ester. This example resulted in an irritation score of 191.

In order to determine whether C12–C15 alkyl benzoates have an effect upon the irritation caused by retinoids in the compositions of this invention, Example 31H was formulated, which contained an excess of C12–C15 alkyl benzoates in the amount of 8% by weight in addition to the 4% by weight present in Example 31A, the control formulation. The irritation score resulting from use of this formulation was 91.

The foregoing examples 31A–31H are oil-in-water emulsion compositions. Example 31I was formulated in order to determine whether an irritation mitigation agent, octyl methoxycinnamate, would be effective to reduce irritation in a water-in-oil emulsion, as follows:

| Ingredient | Control | Formulation 31I |
|---|---|---|
| Disodium EDTA | 0.100 | 0.100 |
| Ascorbic Acid | 0.100 | 0.100 |
| Methyl Paraben | 0.150 | 0.150 |
| Light Mineral Oil | 15.000 | 9.000 |
| Stearyl Alcohol | 5.000 | 5.000 |
| Steareth-21 | 3.250 | 3.250 |
| Steareth-2 | 1.750 | 1.750 |
| BHT | 0.050 | 0.050 |
| Propyl Paraben | 0.100 | 0.100 |
| Zinc Oxide | 5.000 | 5.000 |
| Retinol (45% in Tween ™ 20) | 0.330 | 0.330 |
| Octyl Methoxycinnamate | — | 6.000 |
| Water | 69.170 | 69.170 |

The irritation score for the control formulation was 516 while the Octyl Methoxycinnamate-containing formulation had an irritation score of 240, thus showing an irritation reduction in excess of 50%. Thus, it can be seen that the irritation mitigation agent is effective in reducing irritation notwithstanding the type of delivery system in which the agent is employed.

In Example 31J, below, the control formulation and the composition containing the irritation mitigation agent contained half the amount of retinol as that in Example 31I in order to determine if this factor would reduce the amount of irritation.

EXAMPLE 31J

| Ingredient | Control | Formulation 31J |
|---|---|---|
| Disodium EDTA | 0.100 | 0.100 |
| Ascorbic Acid | 0.100 | 0.100 |
| Methyl Paraben | 0.150 | 0.150 |
| Light Mineral Oil | 15.000 | 9.000 |
| Stearyl Alcohol | 5.000 | 5.000 |
| Steareth-21 | 3.250 | 3.250 |
| Steareth-2 | 1.750 | 1.750 |
| BHT | 0.050 | 0.050 |
| Propyl Paraben | 0.100 | 0.100 |
| Zinc Oxide | 5.000 | 5.000 |
| Retinol (45% in Tween ™ 20) | 0.170 | 0.170 |
| Octyl Methoxycinnamate | — | 6.000 |
| Water | 69.330 | 69.330 |

The irritation score for the control formulation was 269 while the Octyl Methoxycinnamate formulation had an irritation score of 55, thus showing an irritation reduction far in excess of 50%.

Thus, the foregoing examples demonstrate that oil-soluble irritation mitigation agents act to reduce the irritation caused by the retinoid-containing formulations of this invention. The solubility parameter, $\delta$, of the compounds used in Examples 31A–31J above and the difference between $\delta_N$ and $\delta_{RETINOL}$ are set forth in the Table below:

| Compound | $\delta_N$ | $\delta_N - \delta_{RETINOL}$ |
|---|---|---|
| C12 Alkyl Benzoate | 9.25 | −0.31 |
| C15 Alkyl Benzoate | 9.15 | −0.40 |
| Octyl Methoxy Cinnamate | 9.27 | −0.29 |
| Menthyl Anthranilate | 9.69 | 0.13 |
| Homomenthyl Salicylate | 10.7 | 1.14 |
| Octocrylene | 10.3 | 0.74 |
| Octyl Dimethyl PABA | 9.23 | −0.33 |
| TEA Salicylate | 15.4 | 5.84 |
| DEA Methoxysalicylate | 12.5 | 2.94 |
| Retinol | 9.56 | |

What is claimed is:

1. A topical oil-in-water emulsion composition comprising:
   a) an emulsifier system selected from the group consisting of:
      i) a mixture of glyceryl stearate and polyethylene glycol 100 stearate;
      ii) cetearyl alcohol and cetearyl glucoside;
      iii) a mixture of a polyethylene glycol ether of stearyl alcohol of the formula:

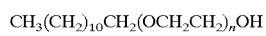
      $CH_3(CH_2)_{10}CH_2(OCH_2CH_2)_nOH$

Wherein n is 21 and a polyethylene glycol ether of stearyl alcohol of the formula:

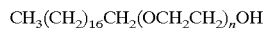
      $CH_3(CH_2)_{16}CH_2(OCH_2CH_2)_nOH$

Wherein n is 2; and
      iv) a mixture of sorbitan stearate and polysorbate 60 (a mixture of stearate esters of sorbitol and sorbitol anhydrides condensed with 20 moles of ethylene oxide);

b) a co-emulsifier selected from the group consisting of cetyl alcohol, stearyl alcohol and mixtures thereof;
c) an oil phase present in the amount of from about 2 to about 20 percent by weight of the total emulsion composition comprising:
   i) a light, dry absorbable oil; and
   ii) substantive, emollient oils or waxes;
wherein said light dry absorbable oil and said substantive oil or wax are present in a ratio of from about 1:3 to about 10:1;
d) vitamin A alcohol; and
e) an irritation mitigating agent wherein said mitigating agent is selected from the group consisting of $C_{12-15}$ alkyl benzoate, octyl methoxycinnamate, octyl dimethyl PABA, octocrylene, menthyl anthranilate, and homomenthyl salicylate present in an irritation mitigation-effective amount, said composition having a pH of from about 4 to about 10.

2. A composition of claim 1, wherein said irritation mitigating agent is octyl methoxycinnamate.

3. A composition of claim 1, wherein said irritation mitigating agent is $C_{12-15}$ alkyl benzoate.

4. A composition of claim 1, wherein said irritation mitigating agent is octyl dimethyl PABA.

5. A composition of claim 1, wherein said irritation mitigating agent is menthyl anthranilate.

6. A composition of claim 2, wherein said composition further comprises $C_{12-15}$ alkyl benzoate.

7. A topical oil-in-water emulsion composition comprising:
a) an emulsifier system selected from the group consisting of:
   i) a mixture of glyceryl stearate and polyethylene glycol 100 stearate;
   ii) cetearyl alcohol and cetearyl glucoside;
   iii) a mixture of a polyethylene glycol ether of stearyl alcohol of the formula:

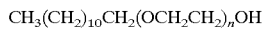

Wherein n is 21 and a polyethylene glycol ether of stearyl alcohol of the formula:

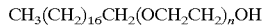

Wherein n is 2 ; and
   iv) a mixture of sorbitan stearate and polysorbate 60 (a mixture of stearate esters of sorbitol and sorbitol anhydrides condensed with 20 moles of ethylene oxide);
b) a co-emulsifier selected from the group consisting of cetyl alcohol, stearyl alcohol and mixtures thereof;
c) vitamin A alcohol; and
d) an irritation mitigating agent wherein said mitigating agent is selected from the group consisting of $C_{12-15}$ alkyl benzoate, octyl methoxycinnamate, octyl dimethyl PABA, octocrylene, menthyl anthranilate, and homomenthyl salicylate present in an irritation mitigation-effective amount.

8. A topical oil-in-water emulsion composition comprising:
a) an emulsifier system selected from the group consisting of:
   i) a mixture of glyceryl stearate and polyethylene glycol 100 stearate;
   ii) cetearyl alcohol and cetearyl glucoside; and
   iii) a mixture of sorbitan stearate and polysorbate 60 (a mixture of stearate esters of sorbitol and sorbitol anhydrides condensed with 20 moles of ethylene oxide);
b) a co-emulsifier selected from the group consisting of cetyl alcohol, stearyl alcohol and mixtures thereof;
c) a retinoid; and
d) an irritation mitigating agent wherein said mitigating agent is selected from the group consisting of $C_{12-15}$ alkyl benzoate, octyl methoxycinnamate, octyl dimethyl PABA, octocrylene, menthyl anthranilate, and homomenthyl salicylate present in an irritation mitigation-effective amount.

9. A composition of claim 8, wherein said retinoid is Vitamin A alcohol.

10. A composition of claim 7, wherein said irritation mitigating agent is octyl methoxycinnamate.

11. A composition of claim 9, wherein said irritation mitigating agent is octyl methoxycinnamate.

12. A composition of claim 7, wherein said irritation mitigating agent is $C_{12-15}$ alkyl benzoate.

13. A composition of claim 9, wherein said irritation mitigation agent is $C_{12-15}$ alkyl benzoate.

14. A composition of claim 10, wherein said irritation mitigating agent is $C_{12-15}$ alkyl benzoate.

15. A composition of claim 11, wherein said irritation mitigating agent is $C_{12-15}$ alkyl benzoate.

16. A composition of claim 1, wherein said emulsifier system is a mixture of glyceryl stearate and polyethylene glycol 100 stearate.

17. A composition of claim 7, wherein said emulsifier system is a mixture of glyceryl stearate and polyethylene glycol 100 stearate.

18. A composition of claim 9, wherein said emulsifier system is a mixture of glyceryl stearate and polyethylene glycol 100 stearate.

19. A composition of claim 1, wherein said an emulsifier system is cetearyl alcohol and cetearyl glucoside.

20. A composition of claim 7, wherein said an emulsifier system is cetearyl alcohol and cetearyl glucoside.

21. A composition of claim 9, wherein said an emulsifier system is cetearyl alcohol and cetearyl glucoside.

22. A topical oil-in-water emulsion composition comprising:
a) an emulsifier system selected from the group consisting of:
   i) a mixture of glyceryl stearate and polyethylene glycol 100 stearate;
   ii) cetearyl alcohol and cetearyl glucoside;
   iii) a mixture of a polyethylene glycol ether of stearyl alcohol of the formula:

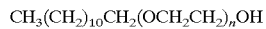

wherein n is 21 and a polyethylene glycol ether of stearyl alcohol of the formula:

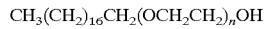

wherein n is 2 ; and
   iv) a mixture of sorbitan stearate and polysorbate 60 (a mixture of stearate esters of sorbitol and sorbitol anhydrides condensed with 20 moles of ethylene oxide);
b) a co-emulsifier selected from the group consisting of cetyl alcohol, stearyl alcohol and mixtures thereof; and
c) vitamin A alcohol.

23. A topical oil-in-water emulsion composition comprising:
   a) an emulsifier system selected from the group consisting of:
      i) a mixture of glyceryl stearate and polyethylene glycol 100 stearate;
      ii) cetearyl alcohol and cetearyl glucoside; and
      iii) a mixture of sorbitan stearate and polysorbate 60 (a mixture of stearate esters of sorbitol and sorbitol anhydrides condensed with 20 moles of ethylene oxide);
   b) a co-emulsifier selected from the group consisting of cetyl alcohol, stearyl alcohol and mixtures thereof; and
   c) a retinoid.

24. A composition of claim 22, wherein said emulsifier system is a mixture of glyceryl stearate and polyethylene glycol 100 stearate.

25. A composition of claim 23, wherein said emulsifier system is a mixture of glyceryl stearate and polyethylene glycol 100 stearate.

26. A composition of claim 22, wherein said an emulsifier system is cetearyl alcohol and cetearyl glucoside.

27. A composition of claim 23, wherein said an emulsifier system is cetearyl alcohol and cetearyl glucoside.

28. A topical oil-in-water emulsion composition comprising:
   a) an emulsifier system comprising a mixture of glyceryl stearate and polyethylene glycol 100 stearate;
   b) a co-emulsifier comprising a mixture of cetyl alcohol and stearyl alcohol; and
   c) vitamin A alcohol.

29. A topical oil-in-water emulsion composition comprising:
   a) an emulsifier system comprising cetearyl alcohol and cetearyl glucoside;
   b) a co-emulsifier comprising cetyl alcohol; and
   c) vitamin A alcohol.

30. A topical oil-in-water emulsion composition comprising:
   a) an emulsifier system comprising a mixture of glyceryl stearate and polyethylene glycol 100 stearate;
   b) a co-emulsifier comprising a mixture of cetyl alcohol and stearyl alcohol;
   c) an oil phase present in the amount of from about 2 to about 20 percent by weight of the total emulsion composition comprising:
      i) a light, dry absorbable oil; and
      ii) substantive, emollient oils or waxes;
   wherein said light dry absorbable oil and said substantive oil or wax are present in a ratio of from about 1:3 to about 10:1; and
   d) vitamin A alcohol.

31. A topical oil-in-water emulsion composition comprising:
   a) an emulsifier system comprising cetearyl alcohol and cetearyl glucoside;
   b) a co-emulsifier comprising cetyl alcohol;
   c) an oil phase present in the amount of from about 2 to about 20 percent by weight of the total emulsion composition comprising:
      i) a light, dry absorbable oil; and
      ii) substantive, emollient oils or waxes;
   wherein said light dry absorbable oil and said substantive oil or wax are present in a ratio of from about 1:3 to about 10:1; and
   e) vitamin A alcohol.

32. The composition of claim 28, wherein said composition further comprises an irritation mitigating agent wherein said irritation mitigating agent is octyl methoxycinnamate.

33. The composition of claim 29, wherein said composition further comprises an irritation mitigating agent wherein said irritation mitigating agent is octyl methoxycinnamate.

34. The composition of claim 30, wherein said composition further comprises an irritation mitigating agent wherein said irritation mitigating agent is octyl methoxycinnamate.

35. The composition of claims 31, wherein said composition further comprises an irritation mitigating agent wherein said irritation mitigating agent is octyl methoxycinnamate.

36. A composition of claim 1, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

37. A composition of claim 7, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

38. A composition of claim 8, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

39. A composition of claim 22, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

40. A composition of claim 23, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

41. A composition of claim 28, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

42. A composition of claim 29, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

43. A composition of claim 30, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

44. A composition of claim 31, wherein the total unsaturation density of the oils in the composition, or C value, of about 1200 or less, wherein C is calculated as follows:

$$C = A \times B,$$

where A is the percentage of an oil or fat in said composition and B is the iodine value of said oil or fat.

* * * * *

UNITED STATES PATENT AND TRADEMARK OFFICE
CERTIFICATE OF CORRECTION

PATENT NO. : 6,461,622 B2
DATED : October 8, 2002
INVENTOR(S) : Liu et al.

It is certified that error appears in the above-identified patent and that said Letters Patent is hereby corrected as shown below:

<u>Title page,</u>
Item [63], Related U.S. Application Data, please insert before Item [51] Int. Cl.:

-- [30] Foreign Application Priority Data
Jul. 9, 1994 [JP] Japan 6-238639 --

Signed and Sealed this

Eighth Day of July, 2003

JAMES E. ROGAN
*Director of the United States Patent and Trademark Office*